(12) United States Patent
Miwa et al.

(10) Patent No.: US 11,696,938 B2
(45) Date of Patent: Jul. 11, 2023

(54) HUMAN CANCER CELL METASTASIS INHIBITORY AGENT AND HUMAN CANCER CELL DETERMINATION AGENT

(71) Applicants: Naofumi Miwa, Tokyo (JP); Mayu Aoyama, Tokyo (JP)

(72) Inventors: Naofumi Miwa, Tokyo (JP); Mayu Aoyama, Tokyo (JP)

(*) Notice: Subject to any disclaimer, the term of this patent is extended or adjusted under 35 U.S.C. 154(b) by 404 days.

(21) Appl. No.: 16/765,757

(22) PCT Filed: Sep. 26, 2018

(86) PCT No.: PCT/JP2018/035776
§ 371 (c)(1),
(2) Date: May 20, 2020

(87) PCT Pub. No.: WO2019/102710
PCT Pub. Date: May 31, 2019

(65) Prior Publication Data
US 2020/0289616 A1  Sep. 17, 2020

(30) Foreign Application Priority Data

Nov. 21, 2017 (JP) .................. 2017-223565

(51) Int. Cl.
| | |
|---|---|
| *A61K 38/17* | (2006.01) |
| *A61P 35/04* | (2006.01) |
| *A61K 38/08* | (2019.01) |
| *A61K 38/10* | (2006.01) |
| *G01N 33/574* | (2006.01) |

(52) U.S. Cl.
CPC .......... *A61K 38/1738* (2013.01); *A61K 38/08* (2013.01); *A61K 38/10* (2013.01); *A61P 35/04* (2018.01); *G01N 33/57484* (2013.01)

(58) Field of Classification Search
CPC ..... A61P 35/04; A61K 38/1738; A61K 38/08; A61K 38/10; A61K 38/05; G01N 33/57484
See application file for complete search history.

(56) References Cited

U.S. PATENT DOCUMENTS

| | | | | |
|---|---|---|---|---|
| 2015/0320848 A1* | 11/2015 | Rammensee | ...... | C07K 14/4748 435/375 |
| 2017/0253633 A1* | 9/2017 | Mahr | ...................... | C07K 16/18 |
| 2018/0141998 A1* | 5/2018 | Nguyen | ................. | G16B 20/50 |

FOREIGN PATENT DOCUMENTS

| | | |
|---|---|---|
| JP | 08-291075 A | 11/1996 |
| JP | 2005-272350 A | 10/2005 |
| JP | 2017-524337 A | 8/2017 |

OTHER PUBLICATIONS

Meng et al. "S100 Calcium Binding Protein A11 (S100A11) Promotes The Proliferation, Migration And Invasion Of Cervical Cancer Cells, And Activates Wnt/ β-Catenin Signaling", OncoTargets and Therapy 2019:12 8675-8685. (Year: 2019).*

Maletzki et al, "S100 Proteins as Diagnostic and Prognostic Markers in Colorectal and Hepatocellular Carcinoma", Hepat Mon. 2012, 16 pages (Year: 2012).*

Cui et al., "Dual effects of targeting S100A11 on suppressing cellular metastatic properties and sensitizing drug response in gastric cancer", Cui et al. Cancer Cell Int (2021) 21:243 (Year: 2021).*

Extended European Search Report for European Patent App. No. 18881761.3 (dated Jul. 2, 2021).

Wang, G., et al., "Colorectal cancer progression correlates with upregulation of S100A11 expression in tumor tissues," Int. J. Colorectal Dis. 2008;23:675-682.

Hao, J., et al., "Selective expression of A100A11 in lung cancer and its role in regulating proliferation of adenocarcinomas cells," Mol. Cell Biochem. 2012;359(1-2):323-332.

Kanamori, T., et al., "Increased expression of calcium-binding protein S100 in human uterine smooth muscle tumours," Molecular Human Reproduction 2004;10(10):735-742.

Hruby, V. J., "Desigining Peptide Receptor Agonists and Antagonists," Nature Rev. Drug Discovery 2002;1(11):847-858.

International Preliminary Report On Patentability for PCT Patent App. No. PCT/JP2018/035776 (dated Jun. 4, 2020).

Hassan, M. S., et al., "A novel intraperitoneal metastatic xenograft mouse model for survival outcome assessment of esophageal adenocarcinoma," PLoS One 2017;12(2):e0171824, pp. 1-13.

Ravindranath, M. H., et al., "Gangliosides of organ-confined versus metastatic androgen-receptor-negative prostate cancer," Biochem. Biophys. Res. Communications 2004;324:154-165.

Bhuiyan, R. H., et al., "Expression analysis of 0-series gangliosides in human cancer cell lines with monoclonal antibodies generated using knockout mice of ganglioside synthase genes," GlycobioL. 2016;26(9):984-998.

Zarei, M., et al., "Separation and identification of GM1b pathway Neu5Ac- and Neu5Gc gangliosides by on-line nanoHPLC-QToF MS and tandem MS: toward glycolipidomics screening of animal cell lines," Glycobiol. 2010;20(1):118-126.

Kroes, R. A., et al., "Overexpression of ST6GaINAcV, a ganglioside-specific alpha2,6-sialylliansferase, inhibits glioma growth in vivo," PNAS 2010;107(28):12646-12651.

Miwa, N., et al., "Dicalcin Inhibits Fertilization through Its Binding to a Glycoprotein in the Egg Envelope in Xenopus laevis," J. Biol. Chem. 2010;285(20):15627-15636.

Hanaue, M., et al., "Characterization of S100A11, a Suppressive Factor of Fertilization, in the Mouse Female Reproductive Tract," Molecular Reproduction & DEvelopment 2011;78:91-103.

Tanaka, M., et al., "Human calgizzarin; one colorectal cancer-related gene selected by a large scale random cDNA sequencing and Northern blot analysis," Cancer Lett. 1995;89:195-200.

(Continued)

*Primary Examiner* — Lianko G Garyu
(74) *Attorney, Agent, or Firm* — Cermak Nakajima & McGowan LLP; Shelly Guest Cermak

(57) ABSTRACT

Provided are a novel agent for inhibiting metastasis of human cancer cells, and a novel agent for determining whether target cells are cancer cells or not in a human. A human cancer cell metastasis inhibitor including human dicalcin or a partial peptide thereof, and a human cancer cell determination agent including human dicalcin or a partial peptide thereof.

4 Claims, 47 Drawing Sheets

Specification includes a Sequence Listing.

(56) References Cited

OTHER PUBLICATIONS

Morimoto, M., "Correlation between the expression of the S100A11 protein and the invasive ability of SW480 colon cancer cells," Ehime Medical Journal 2010;29(2):60-69, with English Abstract.

Cross, S. S., et al., "Expression of S100 proteins in normal human tissues and common cancers using tissue microarrays: S100A6, S100A8, S100A9 and S100A11 are all overexpressed in common cancers," Histopathol. 2005;46:256-269.

Wang, L.-N., et al., "Quantitative Proteome Analysis of Ovarian Cancer Tissues Using a iTRAQ Approach," J. Cell. Biochem. 2012;113:3762-3772.

International Search Report for PCT Patent App. No. PCT/JP2018/035776 (dated Nov. 20, 2018).

\* cited by examiner

|  | p1 | p2 | p3 | p4 | p5 | p6 | p7 |
|---|---|---|---|---|---|---|---|
| Binding ability | − | ++ | − | + | ++ | +++ | ++ |

Fig. 5−10

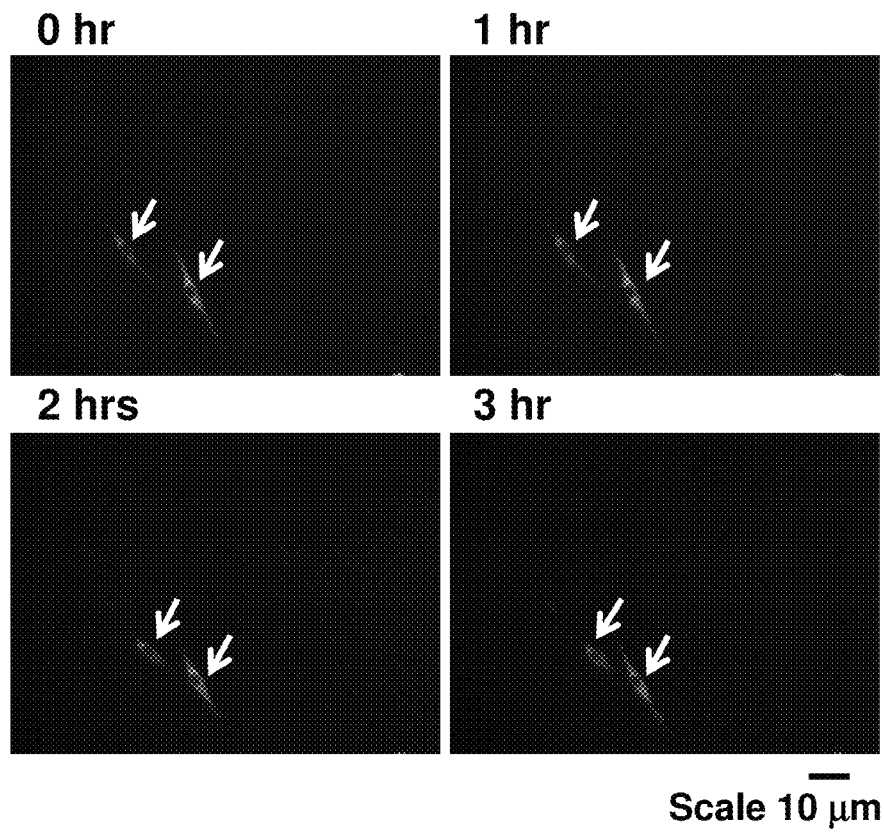
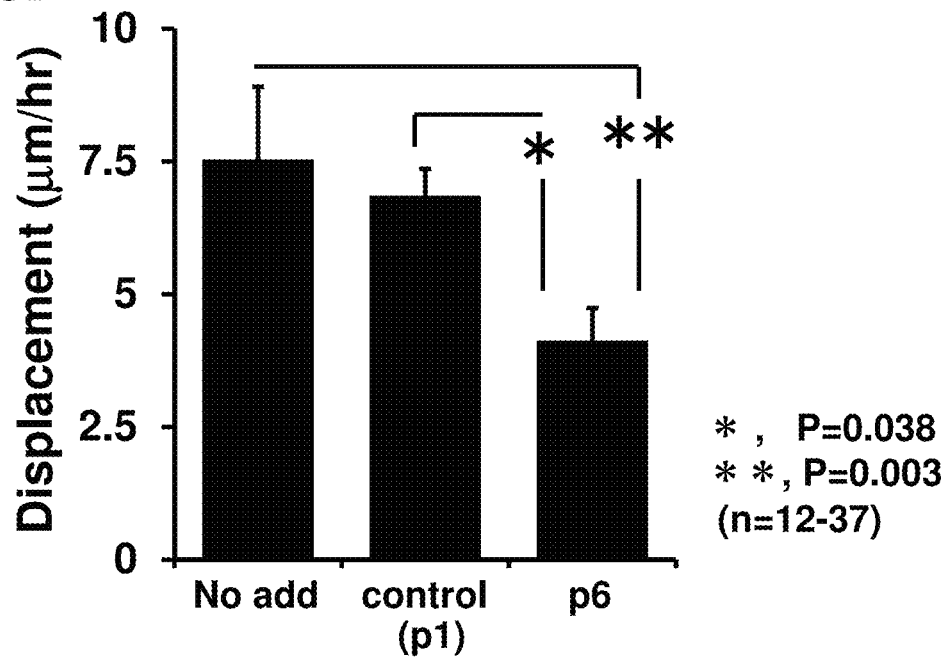

65.3% at 10 μM hDC-p6; *, P=0.03 (n=6)

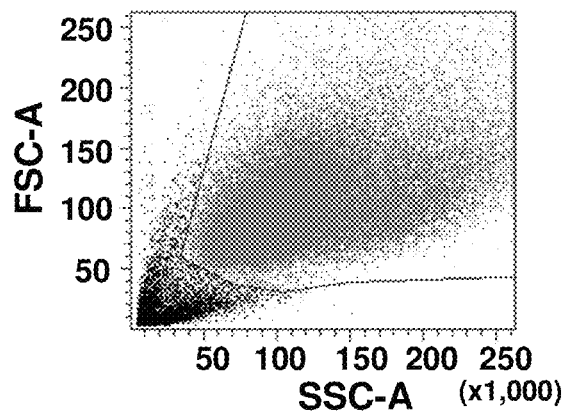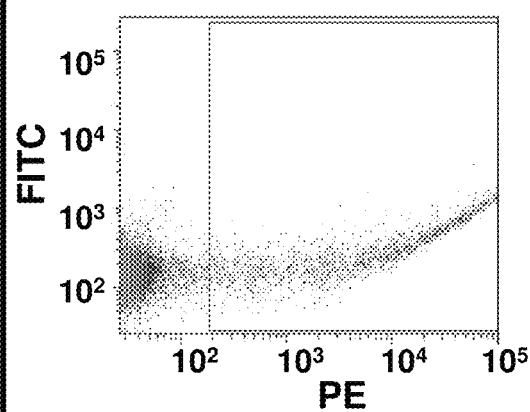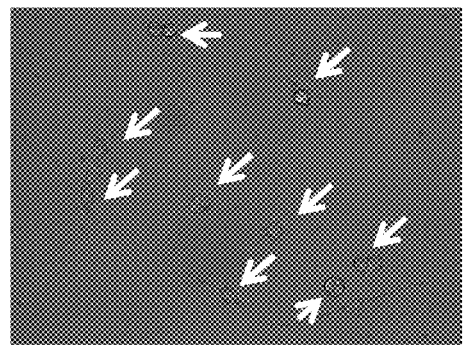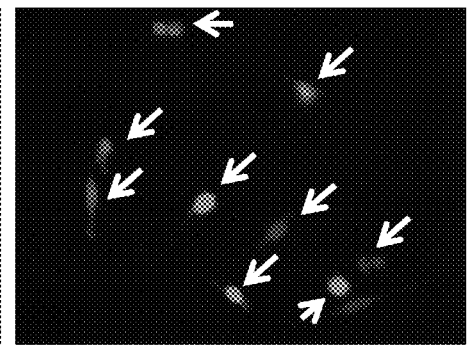

Fig.15-1A
BF tdTomato-OV2944
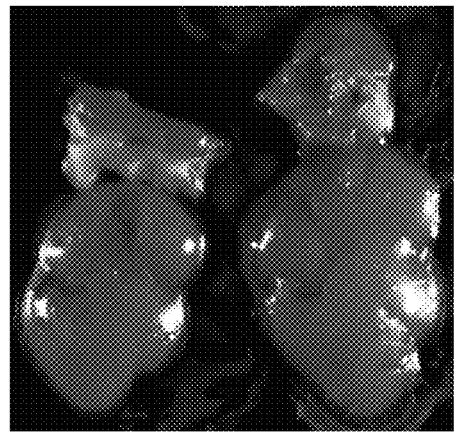
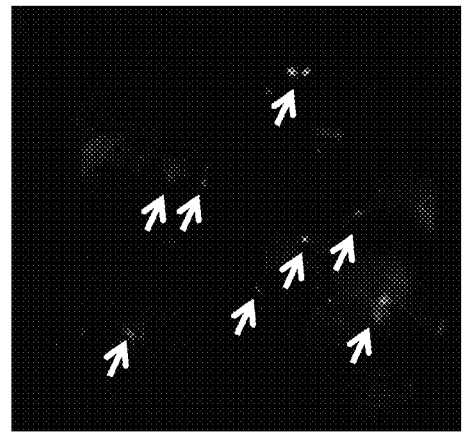
p6  ctrl  1 cm    1 cm
Fig.15-1B
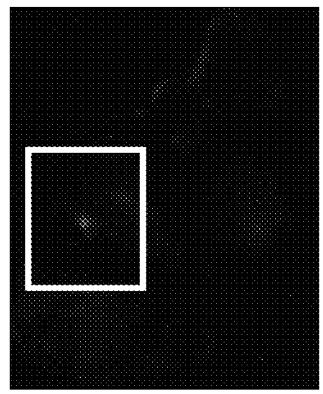
5 mm    5 mm
Fig.15-1C
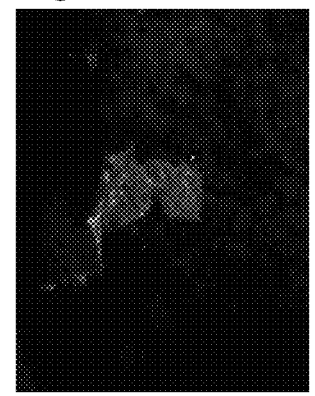
1 mm

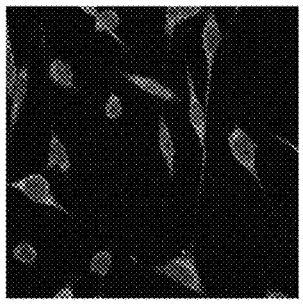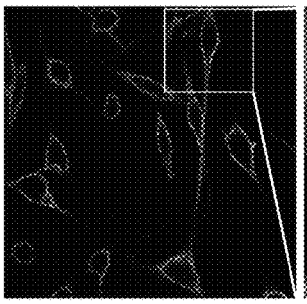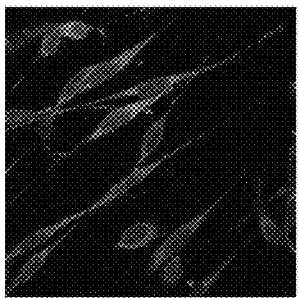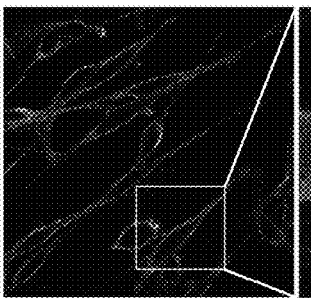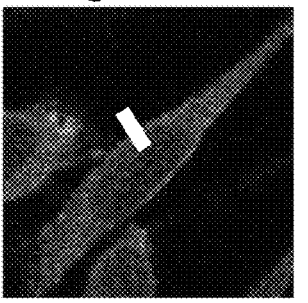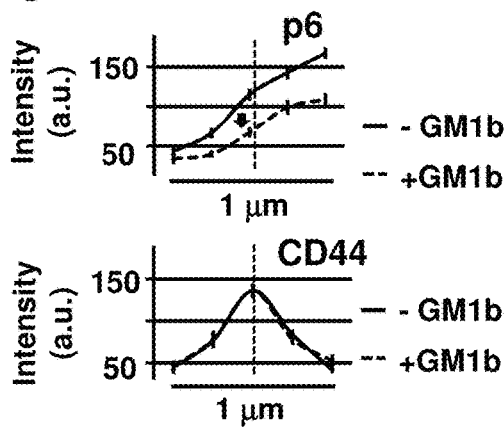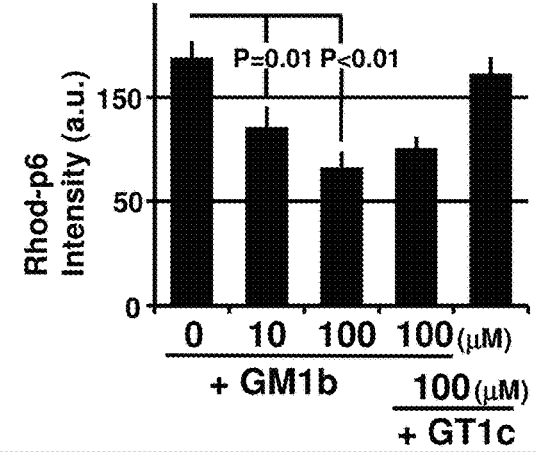

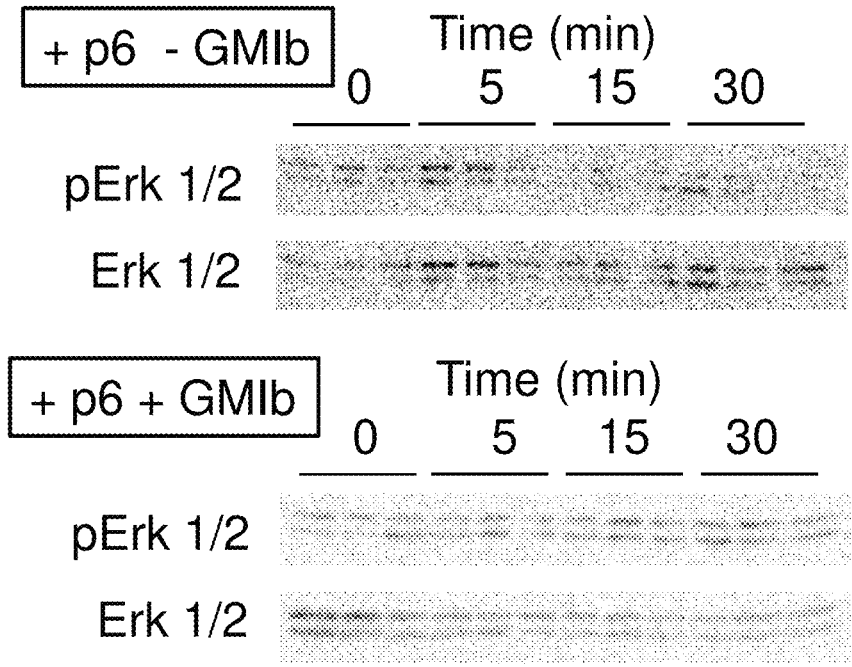
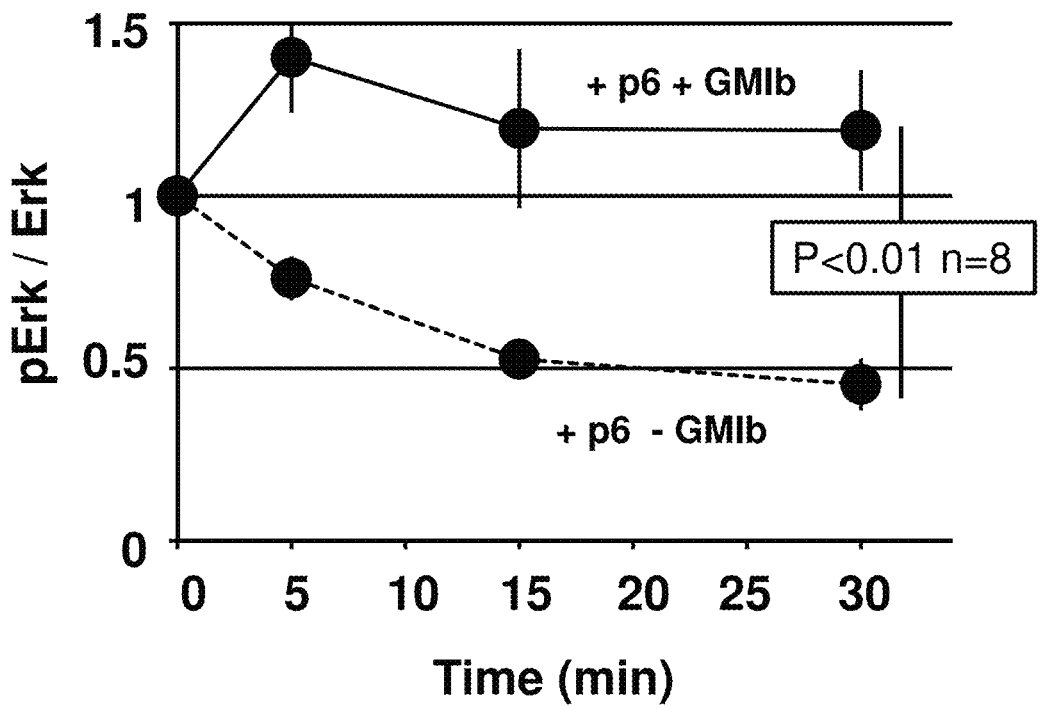

SEQUENCE LISTING

```
<160> NUMBER OF SEQ ID NOS: 20

<210> SEQ ID NO 1
<211> LENGTH: 104
<212> TYPE: PRT
<213> ORGANISM: Homo sapiens

<400> SEQUENCE: 1

Ala Lys Ile Ser Ser Pro Thr Glu Thr Glu Arg Cys Ile Glu Ser Leu
1               5                   10                  15

Ile Ala Val Phe Gln Lys Tyr Ala Gly Lys Asp Gly Tyr Asn Tyr Thr
            20                  25                  30

Leu Ser Lys Thr Glu Phe Leu Ser Phe Met Asn Thr Glu Leu Ala Ala
        35                  40                  45

Phe Thr Lys Asn Gln Lys Asp Pro Gly Val Leu Asp Arg Met Met Lys
    50                  55                  60

Lys Leu Asp Thr Asn Ser Asp Gly Gln Leu Asp Phe Ser Glu Phe Leu
65                  70                  75                  80

Asn Leu Ile Gly Gly Leu Ala Met Ala Cys His Asp Ser Phe Leu Lys
                85                  90                  95

Ala Val Pro Ser Gln Lys Arg Thr
            100

<210> SEQ ID NO 2
<211> LENGTH: 9
<212> TYPE: PRT
<213> ORGANISM: Homo sapiens

<400> SEQUENCE: 2

Pro Thr Glu Thr Glu Arg Cys Ile Glu
1               5
```

<210> SEQ ID NO 3
<211> LENGTH: 9
<212> TYPE: PRT
<213> ORGANISM: Homo sapiens

<400> SEQUENCE: 3

Ser Leu Ile Ala Val Phe Gln Lys Tyr
1               5

<210> SEQ ID NO 4
<211> LENGTH: 18
<212> TYPE: PRT
<213> ORGANISM: Homo sapiens

<400> SEQUENCE: 4

Ala Gly Lys Asp Gly Tyr Asn Tyr Thr Leu Ser Lys Thr Glu Phe Leu
1               5                   10                  15

Ser Phe

<210> SEQ ID NO 5
<211> LENGTH: 20
<212> TYPE: PRT
<213> ORGANISM: Homo sapiens

<400> SEQUENCE: 5

Met Asn Thr Glu Leu Ala Ala Phe Thr Lys Asn Gln Lys Asp Pro Gly
1               5                   10                  15

Val Leu Asp Arg
            20

<210> SEQ ID NO 6
<211> LENGTH: 11
<212> TYPE: PRT
<213> ORGANISM: Homo sapiens

<400> SEQUENCE: 6

Met Met Lys Lys Leu Asp Thr Asn Ser Asp Gly
1               5                   10

<210> SEQ ID NO 7
<211> LENGTH: 11
<212> TYPE: PRT
<213> ORGANISM: Homo sapiens

<400> SEQUENCE: 7

Gln Leu Asp Phe Ser Glu Phe Leu Asn Leu Ile
1               5                   10

<210> SEQ ID NO 8
<211> LENGTH: 21
<212> TYPE: PRT
<213> ORGANISM: Homo sapiens

<400> SEQUENCE: 8

Gly Gly Leu Ala Met Ala Cys His Asp Ser Phe Leu Lys Ala Val Pro
1               5                   10                  15

Ser Gln Lys Arg Thr
            20

<210> SEQ ID NO 9
<211> LENGTH: 15
<212> TYPE: DNA
<213> ORGANISM: Artificial Sequence

```
<220> FEATURE:
<223> OTHER INFORMATION: primer murine 1

<400> SEQUENCE: 9
atgcctacag agact                                                          15

<210> SEQ ID NO 10
<211> LENGTH: 15
<212> TYPE: DNA
<213> ORGANISM: Artificial Sequence
<220> FEATURE:
<223> OTHER INFORMATION: primer murine 2

<400> SEQUENCE: 10
ttagattcgc ttctg                                                          15

<210> SEQ ID NO 11
<211> LENGTH: 97
<212> TYPE: PRT
<213> ORGANISM: Mus musculus

<400> SEQUENCE: 11

Pro Thr Glu Thr Glu Arg Cys Ile Glu Ser Leu Ile Ala Val Phe Gln
1               5                   10                  15

Lys Tyr Ser Gly Lys Asp Gly Asn Asn Thr Gln Leu Ser Lys Thr Glu
            20                  25                  30

Phe Leu Ser Phe Met Asn Thr Glu Leu Ala Ala Phe Thr Lys Asn Gln
        35                  40                  45

Lys Asp Pro Gly Val Leu Asp Arg Met Met Lys Lys Leu Asp Leu Asn
    50                  55                  60

Cys Asp Gly Gln Leu Asp Phe Gln Glu Phe Leu Asn Leu Ile Gly Gly
65                  70                  75                  80

Leu Ala Ile Ala Cys His Asp Ser Phe Ile Gln Thr Ser Gln Lys Arg
                85                  90                  95

Ile

<210> SEQ ID NO 12
<211> LENGTH: 9
<212> TYPE: PRT
<213> ORGANISM: Mus musculus

<400> SEQUENCE: 12

Pro Thr Glu Thr Glu Arg Cys Ile Glu
1               5

<210> SEQ ID NO 13
<211> LENGTH: 9
<212> TYPE: PRT
<213> ORGANISM: Mus musculus

<400> SEQUENCE: 13

Ser Leu Ile Ala Val Phe Gln Lys Tyr
1               5

<210> SEQ ID NO 14
<211> LENGTH: 18
<212> TYPE: PRT
<213> ORGANISM: Mus musculus
```

-continued

<400> SEQUENCE: 14

Ser Gly Lys Asp Gly Asn Asn Thr Gln Leu Ser Lys Thr Glu Phe Leu
1               5                   10                  15

Ser Phe

<210> SEQ ID NO 15
<211> LENGTH: 20
<212> TYPE: PRT
<213> ORGANISM: Mus musculus

<400> SEQUENCE: 15

Met Asn Thr Glu Leu Ala Ala Phe Thr Lys Asn Gln Lys Asp Pro Gly
1               5                   10                  15

Val Leu Asp Arg
            20

<210> SEQ ID NO 16
<211> LENGTH: 11
<212> TYPE: PRT
<213> ORGANISM: Mus musculus

<400> SEQUENCE: 16

Met Met Lys Lys Leu Asp Leu Asn Cys Asp Gly
1               5                   10

<210> SEQ ID NO 17
<211> LENGTH: 11
<212> TYPE: PRT
<213> ORGANISM: Mus musculus

<400> SEQUENCE: 17

Gln Leu Asp Phe Gln Glu Phe Leu Asn Leu Ile
1               5                   10

<210> SEQ ID NO 18
<211> LENGTH: 19
<212> TYPE: PRT
<213> ORGANISM: Mus musculus

<400> SEQUENCE: 18

Gly Gly Leu Ala Ile Ala Cys His Asp Ser Phe Ile Gln Thr Ser Gln
1               5                   10                  15

Lys Arg Ile

<210> SEQ ID NO 19
<211> LENGTH: 22
<212> TYPE: DNA
<213> ORGANISM: Artificial Sequence
<220> FEATURE:
<223> OTHER INFORMATION: primer human 1

<400> SEQUENCE: 19
atggcaaaaa tctccagccc ta                                          22

<210> SEQ ID NO 20
<211> LENGTH: 20
<212> TYPE: DNA
<213> ORGANISM: Artificial Sequence
<220> FEATURE:
<223> OTHER INFORMATION: primer human 2

```
<400> SEQUENCE: 20
ttaggtccgc ttctgggaag                                              20
```

HUMAN CANCER CELL METASTASIS INHIBITORY AGENT AND HUMAN CANCER CELL DETERMINATION AGENT

This application is a national phase entry under 35 U.S.C. § 371 of PCT Patent Application No. PCT/JP2018/035776, filed on Sep. 26, 2018, which claims priority under 35 U.S.C. § 119 to Japanese Patent Application No. 2017-223565, filed Nov. 21, 2017, both of which are incorporated by reference. Also, the Sequence Listing filed electronically herewith is hereby incorporated by reference (File name: 2020-05-20T 250-001 Seq_List; File size: 6 KB; Date recorded: May 20, 2020).

TECHNICAL FIELD

The present invention relates to a human cancer cell metastasis inhibitor and a human cancer cell determination agent.

BACKGROUND ART

Elucidation of the molecular mechanisms of metastasis of cancer cells (malignant tumor cells) from tumor masses to other tissues by hematogenous/lymphatic metastasis or dissemination provides a research basis for cancer, and attempts to find a way for developing the research results into the stage of clinical application have been socially demanded. For example, in ovarian cancer, peritoneal metastasis makes the treatment difficult, and therefore elucidation and control of the molecular mechanism of the metastasis have been medically highly demanded.

Examples of metastasis inhibitors for ovarian cancer include cisplatin, carboplatin, docetaxel, and paclitaxel (Non-patent Document 1), which are major inhibitors; ovarian cancer metastasis inhibitors containing a fullerene as an effective component (Patent Document 1); and ovarian cancer metastasis inhibitors containing an L-ascorbic acid-2-phosphate as an effective component (Patent Document 2). However, protein formulations and peptide formulations are still to be newly developed or improved.

In diagnosis of cancer, pathological diagnosis of cells and tissues plays an important role. In the pathological diagnosis, cells detached from a tissue, or an excised tissue is/are stained, and cancer cells are observed under the microscope. Thus, it is thought that development of a staining method that contributes to identification of cancer cells may increase the determination accuracy in the pathological diagnosis, and may contribute to diagnosis and treatment of cancers.

Ganglioside is a family of several ten kinds of glycolipids, and present on the plasma membrane (especially on lipid rafts). Ganglioside acts to activate receptors that receive extracellular signals, and influences downstream intracellular signaling systems such as Erk1/2, to be involved in various cellular events including cell migration. In particular, GM1b ganglioside is known to be expressed in, for example, the prostate cancer cell line HH870, the retinoblastoma cell line Y79, and the lymphoma cell line YAC-1 (Non-patent Documents 2 to 4). Further, since cancer cell invasion in vitro is suppressed when the expression level of GM1b is low, it has been suggested that GM1b may affect cancer intracellular signaling, to enhance the cell migration ability and the metastatic ability (Non-patent Document 5).

On the other hand, a substance called dicalcin (DC), which is a factor that regulates the fertilization efficiency, has been identified from *Xenopus laevis* eggs (Non-patent Document 6). Dicalcin is known to bind to a glycoprotein constituting the egg envelope (extracellular matrix surrounding the egg), to control the orientation of the extracellular matrix filaments throughout the egg envelope. Further, molecular phylogenetic analysis of dicalcin in mammals revealed that S100A11 is its homologous protein (Non-patent Document 7). Dicalcin (S100A11) is a member of the S100 protein family, which is a low-molecular-weight calcium-binding protein. It is known to be present in human, mouse, pig, and the like.

PRIOR ART DOCUMENTS

Patent Documents

Patent Document 1: JP 2005-272350 A
Patent Document 2: JP H08-291075 A

Non-Patent Documents

Non-patent Document 1: Hassan M S, et al., PLoS ONE, 12(2): e0171824(2017)
Non-patent Document 2: Ravindranath M H, et al., Biochem. Biophys. Res. Commun., 5, 324(1), 154-65 (2004)
Non-patent Document 3: Bhuiyan R H, et al., Glycobiology, 26(9), 984-998 (2016)
Non-patent Document 4: Zarei M, et al., Glycobiology, 20(1), 118-26 (2010)
Non-patent Document 5: Kroes R A, et al., Proc. Natl. Acad. Sci. U.S.A., 107(28), 12646-51 (2010)
Non-patent Document 6: Miwa, et al., J. Biol. Chem., 285, 15627-15636 (2010)
Non-patent Document 7: Hanaue, et al., Mol. Reprod. Dev., 78, 91-103 (2011)

SUMMARY OF THE INVENTION

Problems to be Solved by the Invention

An object of the present invention is to provide a novel agent that inhibits metastasis of human cancer cells, preferably an agent that exerts an effect even at a lower dose compared to conventional metastasis inhibitors. Another object of the present invention is to provide a novel agent for determining whether target cells are cancer cells or not in a human, preferably an agent with which the determination can be carried out in a short time.

Means for Solving the Problems

The present inventors searched for, and improved, novel substances that inhibit metastasis of human cancer cells, to discover that human dicalcin or a partial peptide thereof effectively inhibits metastasis of human cancer cells. Further, the present inventors discovered that, since the human dicalcin or partial peptide thereof binds to the human cancer cells upon the inhibition of metastasis of the cancer cells, it is useful for judging whether target cells are cancer cells are not, thereby completing the present invention. The present invention is as follows.

[1] A human cancer cell metastasis inhibitor comprising human dicalcin or a partial peptide thereof.
[2] The inhibitor according to [1], wherein the human dicalcin has the amino acid sequence of SEQ ID NO:1.
[3] The inhibitor according to [1], wherein the partial peptide is a partial peptide which has one amino acid sequence selected from SEQ ID NOs:3, 5, 6, 7, and 8, and which has human cancer cell metastasis inhibitory activity, or a partial peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which has human cancer cell metastasis inhibitory activity.

[4] The inhibitor according to any one of [1] to [3], wherein the cancer cell is a cell(s) of one or more cancers and/or tumors selected from the group consisting of ovarian cancer, prostate cancer, colorectal cancer, breast cancer, renal cancer, lung cancer, glioma, retinoblastoma, and lymphoma.

[5] A peptide which has one amino acid sequence selected from SEQ ID NOs:3, 5, 6, 7, and 8, and which has human cancer cell metastasis inhibitory activity, a peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which has human cancer cell metastasis inhibitory activity, or a pharmaceutically acceptable salt thereof.

[6] A human cancer cell determination agent comprising human dicalcin or a partial peptide thereof.

[7] The determination agent according to [6], wherein the human dicalcin has the amino acid sequence of SEQ ID NO:1.

[8] The determination agent according to [6], wherein the partial peptide is a partial peptide which has one amino acid sequence selected from SEQ ID NOs:3, 5, 6, 7, and 8, and which binds to a human cancer cell, or a partial peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which binds to a human cancer cell.

[9] The determination agent according to any one of [6] to [8], wherein the cancer cell is a cell(s) of one or more cancers and/or tumors selected from the group consisting of ovarian cancer, prostate cancer, colorectal cancer, breast cancer, renal cancer, lung cancer, glioma, retinoblastoma, and lymphoma.

[10] A peptide which has one amino acid sequence selected from SEQ ID NOs:3, 5, 6, 7, and 8, and which binds to a human cancer cell, a peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which binds to a human cancer cell, or a pharmaceutically acceptable salt thereof.

Effect of the Invention

According to the present invention, a novel agent for inhibiting metastasis of human cancer cells can be provided. The agent exerts an effect even at a lower dose than conventional human cancer cell metastasis inhibitors. Further, according to the present invention, a novel agent for determining whether target cells are cancer cells or not in a human can be provided. The agent exerts an effect that enables the determination in a short time.

BRIEF DESCRIPTION OF THE DRAWINGS

FIG. 1-2 shows confocal micrographs in one experimental example in the present invention (drawing-substituting photographs).

FIG. 1-3 shows confocal micrographs in one experimental example in the present invention (drawing-substituting photographs).

FIG. 2 shows a graph illustrating the results of a cell invasion assay in one experimental example in the present invention.

FIG. 3 shows a graph illustrating the results of a cell adhesion assay in one experimental example in the present invention.

FIG. 5-1 shows a diagram illustrating the positions of partial peptides p1 to p7 along the full-length mouse dicalcin in one experimental example in the present invention.

FIG. 5-2 shows confocal micrographs in one experimental example in the present invention (drawing-substituting photographs).

FIG. 5-3 shows confocal micrographs in one experimental example in the present invention (drawing-substituting photographs).

FIG. 5-4 shows confocal micrographs in one experimental example in the present invention (drawing-substituting photographs).

FIG. 5-5 shows confocal micrographs in one experimental example in the present invention (drawing-substituting photographs).

FIG. 5-6 shows confocal micrographs in one experimental example in the present invention (drawing-substituting photographs).

FIG. 5-7 shows confocal micrographs in one experimental example in the present invention (drawing-substituting photographs).

FIG. 5-8 shows confocal micrographs in one experimental example in the present invention (drawing-substituting photographs).

FIG. 5-9 shows confocal micrographs in one experimental example in the present invention (drawing-substituting photographs).

FIG. 5-10 shows a graph illustrating the results of a cell binding experiment in one experimental example in the present invention.

FIG. 6 shows a graph illustrating the results of a cell invasion assay in one experimental example in the present invention.

FIG. 7 shows a graph illustrating the results of a cell invasion assay in one experimental example in the present invention.

FIG. 8A shows the results of a cell migration assay in one experimental example in the present invention and shows fluorescence micrographs (drawing-substituting photographs).

FIG. 8B shows the results of a cell migration assay in one experimental example in the present invention and shows a graph illustrating results on the migration distance.

FIG. 9 shows a graph illustrating the results of a cell invasion assay in one experimental example in the present invention.

FIG. 10 shows a graph illustrating the results of a cell survival assay in one experimental example in the present invention.

FIG. 11-1 shows confocal micrographs in a cell binding experiment in one experimental example in the present invention (drawing-substituting photographs).

FIG. 11-2 shows confocal micrographs in a cell binding experiment in one experimental example in the present invention (drawing-substituting photographs).

FIG. 12-1 shows a graph illustrating the results of a cell invasion assay in one experimental example in the present invention.

FIG. 12-2 shows confocal micrographs in a cell binding experiment in one experimental example in the present invention (drawing-substituting photographs).

FIG. 12-3 shows a graph illustrating the results of a cell invasion assay in one experimental example in the present invention.

FIG. 13A shows diagrams presenting information on the mouse ovarian tumor cell line OV2944 cells expressing the fluorescent protein tdTomato, prepared in one experimental example in the present invention and shows the results of FACS for the fluorescent protein tdTomato.

FIG. 13B shows diagrams presenting information on the mouse ovarian tumor cell line OV2944 cells expressing the fluorescent protein tdTomato, prepared in one experimental example in the present invention and shows the results of FACS for the fluorescent protein tdTomato.

FIG. 13C shows diagrams presenting information on the mouse ovarian tumor cell line OV2944 cells expressing the fluorescent protein tdTomato, prepared in one experimental example in the present invention and shows a fluorescence micrograph of OV2944 cells expressing tdTomato (drawing-substituting photograph).

FIG. 15-1A shows stereomicrographs of tdTomato-expressing OV2944 cells in a liver in one experimental example in the present invention (drawing-substituting photographs) and shows images illustrating comparison of mouse livers after injection of partial peptide p6 or control peptide p1.

FIG. 15-1B shows stereomicrographs of tdTomato-expressing OV2944 cells in a liver in one experimental example in the present invention (drawing-substituting photographs) and shows images depicting colonies of tdTomato-expressing OV2944 cells.

FIG. 15-1C shows stereomicrographs of tdTomato-expressing OV2944 cells in a liver in one experimental example in the present invention (drawing-substituting photographs) and shows a magnified image of the area surrounded by the white square in the fluorescence image in FIG. 15-1B.

FIG. 15-2 shows a graph illustrating the result on the colony number of tdTomato-expressing OV2944 cells in a liver in one experimental example in the present invention.

FIG. 16-1 shows a graph illustrating the result of survival analysis of mice in one experimental example in the present invention.

FIG. 16-2 shows a graph illustrating the result of survival analysis of mice in one experimental example in the present invention.

FIG. 17-1 shows a fluorescence micrograph illustrating binding of a peptide to cells in one experimental example in the present invention (drawing-substituting photograph).

FIG. 17-2 shows a fluorescence micrograph illustrating binding of a peptide to cells in one experimental example in the present invention (drawing-substituting photograph).

FIG. 17-3 shows a fluorescence micrograph illustrating binding of a peptide to cells in one experimental example in the present invention (drawing-substituting photograph).

FIG. 17-4 shows a fluorescence micrograph illustrating binding of a peptide to cells in one experimental example in the present invention (drawing-substituting photograph).

FIG. 17-5 shows a fluorescence micrograph illustrating binding of a peptide to cells in one experimental example in the present invention (drawing-substituting photograph).

FIG. 17-6 shows a fluorescence micrograph illustrating binding of a peptide to cells in one experimental example in the present invention (drawing-substituting photograph).

FIG. 17-7 shows a fluorescence micrograph illustrating binding of a peptide to cells in one experimental example in the present invention (drawing-substituting photograph).

FIG. 17-8 shows a fluorescence micrograph illustrating binding of a peptide to cells in one experimental example in the present invention (drawing-substituting photograph).

FIG. 17-9 shows a fluorescence micrograph illustrating binding of a peptide to cells in one experimental example in the present invention (drawing-substituting photograph).

FIG. 17-10 shows a fluorescence micrograph illustrating binding of a peptide to cells in one experimental example in the present invention (drawing-substituting photograph).

FIG. 17-11 shows a fluorescence micrograph illustrating binding of a peptide to cells in one experimental example in the present invention (drawing-substituting photograph).

FIG. 17-12 shows a fluorescence micrograph illustrating binding of a peptide to cells in one experimental example in the present invention (drawing-substituting photograph).

FIG. 19A shows the results of a peptide binding inhibition assay in one experimental example in the present invention and shows confocal micrographs (drawing-substituting photographs).

FIG. 19B shows the results of a peptide binding inhibition assay in one experimental example in the present invention and shows confocal micrographs (drawing-substituting photographs).

FIG. 19C shows the results of a peptide binding inhibition assay in one experimental example in the present invention and shows graphs illustrating the relationship between the fluorescence intensity measurement position and the fluorescence intensity.

FIG. 19D shows the results of a peptide binding inhibition assay in one experimental example in the present invention and shows a graph illustrating the relationship between the GM1b and/or GT1c concentration(s) and the fluorescence intensity.

FIG. 20A shows the results of an experiment on the activation of Erk1/2 protein in one experimental example in the present invention and shows Western blot images (drawing-substituting photographs).

FIG. 20B shows the results of an experiment on the activation of Erk1/2 protein in one experimental example in the present invention and shows a graph illustrating the relationship between the reaction time and the ratio of pErk to Erk (pErk/Erk).

MODE FOR CARRYING OUT THE INVENTION

Figure 1:
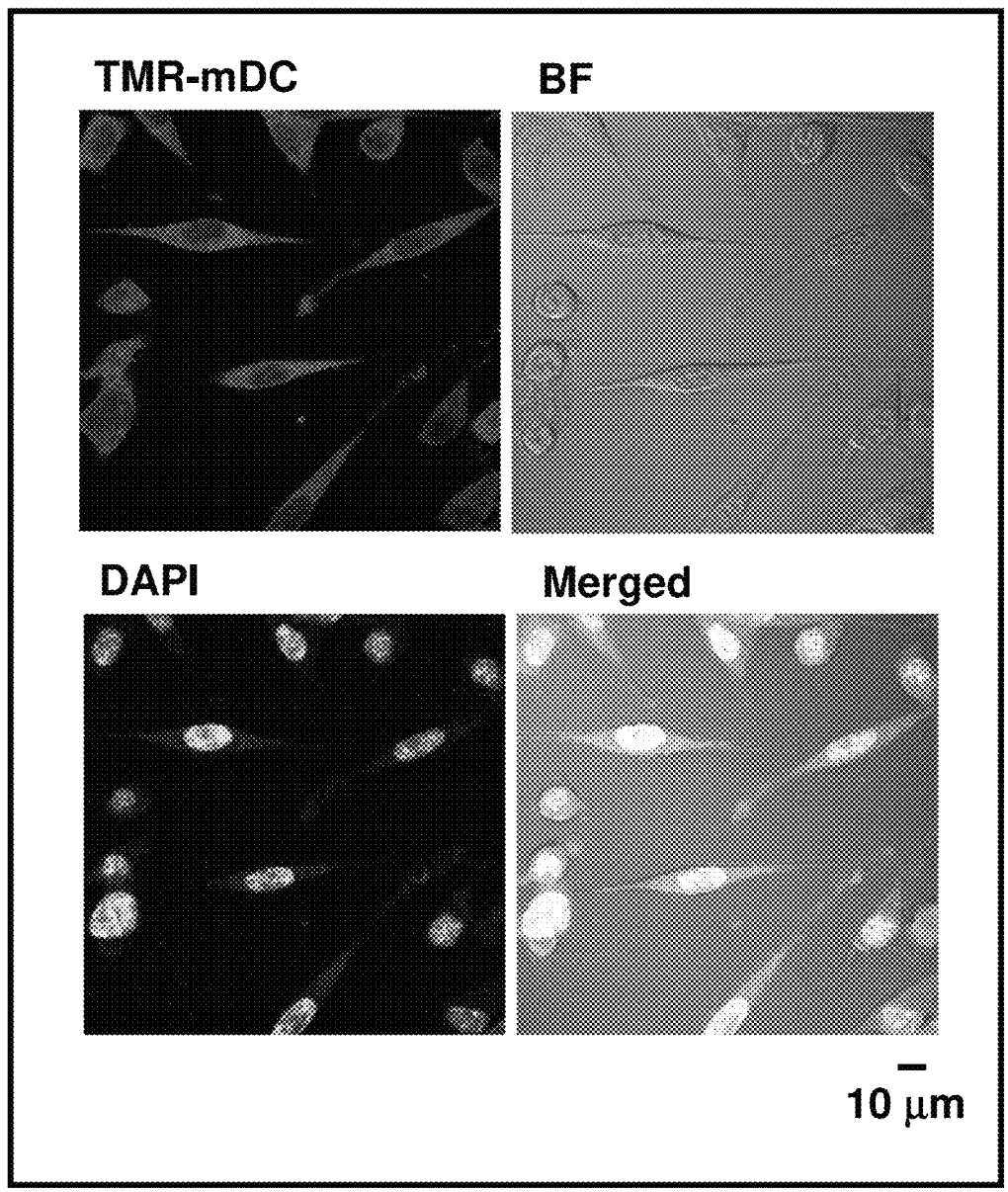
FIG. 1-1 shows confocal micrographs in one experimental example in the present invention (drawing-substituting photographs).

One embodiment of the present invention is a human cancer cell metastasis inhibitor comprising human dicalcin or a partial peptide thereof.

The human dicalcin contained in the human cancer cell metastasis inhibitor of the present embodiment is not limited as long as the human dicalcin has an activity that inhibits metastasis of human cancer cells. The human dicalcin may be, for example, human dicalcin having the amino acid sequence of SEQ ID NO:1, or having an amino acid sequence having an identity of not less than 80%, preferably not less than 90%, more preferably not less than 95% to the amino acid sequence of SEQ ID NO:1.

The partial peptide of human dicalcin is not limited as long as it has a human cancer cell metastasis inhibitory activity. The partial peptide is preferably a partial peptide having one amino acid sequence selected from SEQ ID NOs:3, 5, 6, 7, and 8, which correspond to hDC-p2, 4, 5, 6, and 7 in Examples, respectively; more preferably a partial peptide having one amino acid sequence selected from SEQ ID NOs:3, 6, 7, and 8, which correspond to hDC-p2, 5, 6, and 7 in Examples, respectively; still more preferably a partial peptide having the amino acid sequence of SEQ ID No:7, which corresponds to hDC-p6 in Examples.

The partial peptide may also be a partial peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which has human cancer cell metastasis inhibitory activity. "One or several" means preferably one to three, more preferably one or two, still more preferably one. The same applies to cases where an amino acid(s) is/are added to the N-terminal side and/or the C-terminal side.

The substitution is preferably conservative substitution. The conservative substitution means substitution among Phe, Trp, and Tyr in cases where the substitution site has an aromatic amino acid; substitution among Leu, Ile, and Val in cases where the substitution site has a hydrophobic amino acid; substitution between Gln and Asn in cases where the substitution site has a polar amino acid; substitution among Lys, Arg, and His in cases where the substitution site has a basic amino acid; substitution between Asp and Glu in cases where the substitution site has an acidic amino acid; or substitution between Ser and Thr in cases where the substitution site has an amino acid containing a hydroxyl group. Specific examples of the conservative substitution include substitution from Ala to Ser or Thr; substitution from Arg to Gln, His, or Lys; substitution from Asn to Glu, Gln, Lys, His, or Asp; substitution from Asp to Asn, Glu, or Gln; substitution from Cys to Ser or Ala; substitution from Gln to Asn, Glu, Lys, His, Asp, or Arg; substitution from Glu to Gly, Asn, Gln, Lys, or Asp; substitution from Gly to Pro; substitution from His to Asn, Lys, Gln, Arg, or Tyr; substitution from Ile to Leu, Met, Val, or Phe; substitution from Leu to Ile, Met, Val, or Phe; substitution from Lys to Asn, Glu, Gln, His, or Arg; substitution from Met to Ile, Leu, Val, or Phe; substitution from Phe to Trp, Tyr, Met, Ile, or Leu; substitution from Ser to Thr or Ala; substitution from Thr to Ser or Ala; substitution from Trp to Phe or Tyr; substitution from Tyr to His, Phe, or Trp; and substitution from Val to Met, Ile, or Leu.

The amino acid sequence inserted is not limited as long as the human cancer cell metastasis inhibitory activity is maintained. Regarding the amino acid sequence added, as long as the human cancer cell metastasis inhibitory activity is maintained, an amino acid sequence having a different origin may be added so as to provide, for example, a fluorescent protein, or a tag protein to be used for quantification of expression or separation. By providing the fluorescent protein, the protein can be traced. By providing the tag protein, separation, purification, and the like are possible therewith. Any of these may be carried out according to a conventional method.

An amino acid sequence selectively delivered to a tissue in which target cancer cells are present may be added to the human dicalcin or partial peptide thereof. By the addition of such a sequence, the effect of the present embodiment can be exerted only for the target cancer cells without damaging normal cells.

The human dicalcin or partial peptide thereof may be modified. Examples of the modification include amidation, lipid chain addition (such as fatty acylation (palmitoylation, myristoylation, or the like) or prenylation (farnesylation, geranylgeranylation, or the like)), phosphorylation (phosphorylation in a serine residue, threonine residue, tyrosine residue, or the like), acetylation, and sugar chain addition (N-glycosylation, O-glycosylation, or the like).

The method of obtaining the human dicalcin or partial peptide thereof is not limited, and examples of the method include conventional genetic engineering methods and molecular biological methods. For example, a recombinant expression vector encoding the human dicalcin or partial peptide thereof may be prepared and introduced into a host, and may then be expressed, followed by purification to obtain the human dicalcin or partial peptide thereof. The human dicalcin or partial peptide thereof may also be obtained by peptide synthesis.

The human cancer cell metastasis inhibitor of the present embodiment may contain either a single kind or a plurality of kinds of the human dicalcin and/or partial peptide thereof. The inhibitor may be formulated by employing a known formulation method based on mixing with a known pharmaceutically acceptable carrier and/or the like.

Examples of the formulation materials include surfactants, excipients, coloring agents, flavoring agents, preservatives, stabilizers, buffers, suspending agents, isotonic agents, binders, disintegrating agents, lubricants, fluidizers, and flavoring agents. Without being restricted by these, known carriers may be used. Specific examples of the carriers include light anhydrous silicic acid, lactose, crystalline cellulose, mannitol, starch, carmellose calcium, carmellose sodium, hydroxypropyl cellulose, hydroxypropyl methylcellulose, polyvinylacetal diethylaminoacetate, polyvinylpyrrolidone, gelatin, medium-chain triglyceride, saccharose, carboxymethyl cellulose, corn starch, and inorganic salts.

Examples of the human cancer cells include cancer cells or tumor cells in ovarian cancer, prostate cancer, colorectal cancer (such as rectal cancer or colon cancer), breast cancer (such as breast ductal carcinoma, invasive lobular carcinoma, mucinous carcinoma, or medullary carcinoma), renal cancer, lung cancer (such as small cell carcinoma), glioma, retinoblastoma, lymphoma, liver cancer, pancreatic cancer, gastric cancer, uterine cancer, laryngeal cancer, pharyngeal cancer, tongue cancer, or the like. In particular, cancer cells or tumor cells in ovarian cancer, prostate cancer, colorectal cancer (such as rectal cancer or colon cancer), breast cancer (such as breast ductal carcinoma, invasive lobular carcinoma, mucinous carcinoma, or medullary carcinoma), renal cancer, lung cancer (such as small cell carcinoma), glioma, retinoblastoma, or lymphoma are preferred.

Ganglioside is present mainly on lipid rafts on the plasma membrane, and acts to activate receptors that receive extracellular signals, to affect downstream intracellular signaling systems. According to Non-patent Document 5, cancer cell invasion is suppressed when the expression level of GM1b is decreased in cancer cells. Therefore, it is known that, in the cancer cells, GM1b enhances Erk1/2 activation, leading to enhancement of the cell migration ability and the metastatic ability. As described in Examples in the present description, it was suggested that partial peptide p6 of mouse dicalcin binds to GM1b on the cancer cell plasma membrane. It is thus thought that the binding inhibits the Erk1/2 activation caused by GM1b, and hence inhibits the metastasis-enhancing action due to the activation, resulting in suppression of the cell migration ability and the metastatic ability of the cancer cells to which the human dicalcin or partial peptide thereof is bound.

The human cancer cell metastasis inhibitor of the present embodiment may be in either a powder form or liquid form, or an appropriate dosage form other than these may be selected. In cases where the inhibitor is in a liquid form, the content of the human dicalcin or partial peptide thereof with respect to the total amount is not limited as long as metastasis of human cancer cells can be inhibited. From the viewpoint of convenience in the dissolution, storage, and the like, the total amount the human dicalcin or partial peptide thereof is preferably not less than 0.04 mg/mL, more preferably not less than 0.8 mg/mL, still more preferably not less than 4 mg/mL, and on the other hand, preferably not more than 500 mg/mL, more preferably not more than 200 mg/mL, still more preferably not more than 50 mg/mL. As formulation materials such as a solvent, those used for conventional pharmaceuticals may be used.

The method of application of the human cancer cell metastasis inhibitor of the present embodiment to a human may be either oral administration or parenteral administration. The method is preferably parenteral administration, more preferably administration by injection. Examples of the administration by injection include intraperitoneal injection, intravenous injection, intramuscular injection, and subcutaneous injection. These enable systemic or local administration. Further, the administration method may be appropriately selected according to the age and the symptoms of the patient.

The dose may be appropriately selected according to, for example, the age and/or body weight of the patient, symptoms, administration schedule, formulation, and/or level of the inhibitory activity. Since the human cancer cell metastasis inhibitor of the present embodiment exerts an equivalent effect at a lower dose than conventional agents such as paclitaxel, the dose is, for example, preferably not less than 0.05 mg/kg, more preferably not less than 0.1 mg/kg, still more preferably not less than 0.2 mg/kg, and on the other hand, preferably not more than 15 mg/kg, more preferably not more than 5 mg/kg, still more preferably not more than 1 mg/kg, in terms of the every-other-day dose per kg body weight. The administration schedule does not necessarily need to be the every-other-day schedule, and may be an administration schedule that gives a dose within the range described above when the dose is calculated in terms of the every-other-day dose. The dose to be administered in one day may be administered dividedly in several times in the one day.

Another embodiment of the present invention is a peptide which has one amino acid sequence selected from SEQ ID NOs:3, 5, 6, 7, and 8, and which has human cancer cell metastasis inhibitory activity, a peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which has human cancer cell metastasis inhibitory activity, or a pharmaceutically acceptable salt thereof.

For their details, the descriptions for the above embodiment are applied.

The pharmaceutically acceptable salt employed may be a salt with, for example, a pharmaceutically acceptable acid (such as an inorganic acid or organic acid) or base (such as an alkali metal salt). A pharmaceutically acceptable acid addition salt is preferred. Examples of such a salt include salts with an inorganic acid (such as hydrochloric acid, phosphoric acid, hydrobromic acid, or sulfuric acid), and salts with an organic acid (such as acetic acid, formic acid, propionic acid, fumaric acid, maleic acid, succinic acid, tartaric acid, citric acid, malic acid, oxalic acid, benzoic acid, methanesulfonic acid, or benzenesulfonic acid). These pharmaceutically acceptable salts may be produced by known methods.

Another embodiment of the present invention is a human cancer cell determination agent containing human dicalcin or a partial peptide thereof.

As described in Examples, partial peptide hDC-p6 of human dicalcin binds to human cancer cells. Thus, since cells to which the human dicalcin or partial peptide thereof binds can be judged as cancer cells, the human dicalcin or partial peptide thereof is useful as a human cancer cell determination agent.

The target cells may be cells to be judged regarding whether the cells are cancer cells are not, and may be desired cells. Preferably, for example, the cells may be cells collected from a human for pathological examination or the like, or may be uncollected living cells themselves. The collection method for collecting the cells from a human may be a method in accordance with a conventional method. In cases where living cells are to be targeted as they are without collection of the cells from a human, for example, a spray-type method in which the determination agent is sprayed to a target site may be employed.

The binding of the human dicalcin or partial peptide thereof to cells may be detected by a conventional method for detection of binding of a protein or partial peptide thereof to cells. In cases where cells collected from a human are to be targeted, examples of the detection include immunocytostaining, immunohistochemical staining, thin layer chromatography, and Western blotting. In cases where living cells are to be targeted without collection of the cells from a human, examples of the detection include vital staining and fluorescence staining.

For the human dicalcin, partial peptide thereof, and human cancer cells, the descriptions for the above embodiment are applied except for the following.

The content of the human dicalcin or partial peptide thereof with respect to the total amount of the human cancer cell determination agent of the present embodiment is not limited as long as whether the target human cells are cancer cells or not can be determined. When used, the total amount (final concentration) of the human dicalcin or partial peptide thereof is preferably not less than 0.1 µg/mL, more preferably not less than 0.2 µg/mL, still more preferably not less than 0.5 µg/mL, and on the other hand, preferably not more than 50 µg/mL, more preferably not more than 20 µg/mL, still more preferably not more than 5 µg/mL. The concentration during a period when the agent is not used, for example, during storage, may be, for example, 10 to 1000 times higher than this range.

Another embodiment of the present invention is a method of determining whether cells are cancer cells or not, the method including a step of detecting binding of the human dicalcin or partial peptide thereof to the cells.

The method preferably uses the determination agent. For its details, the descriptions for the embodiment of the determination agent are applied.

Another embodiment of the present invention is a kit for determining whether cells are cancer cells or not (human cancer cell determination kit), the kit including the following component (A) or (B):

(A) A human dicalcin or partial peptide thereof; or (B) a peptide which has one amino acid sequence selected from SEQ ID NOs:3, 5, 6, 7, and 8, and which binds to a human cancer cell, a peptide which has the same amino acid sequence as one amino acid sequence selected from SEQ ID NOs:3, 5, 6, 7, and 8 except that one or several amino acids are substituted and/or deleted, and/or one or several amino acids are inserted and/or added, and which binds to a human cancer cell, or a pharmaceutically acceptable salt thereof;

wherein, for the details, the descriptions for the above embodiments are applied.

In cases where a plurality of solvents and/or solutions are contained for either (A) or (B), they may be contained as a mixed solvent or mixed solution in one container, or may be contained in separate containers.

Regarding preferred types and concentrations, conditions for use, and the like, the conditions described for the determination agent and the determination method may be used for both (A) and (B). The solvents and/or solutions may be concentrated as appropriate before use, and may be diluted as appropriate with sterile water or the like immediately before use.

The kit may also include, for example, instructions describing the determination method.

EXAMPLES

The present invention is described below more concretely by way of Examples. However, the present invention is not limited to the following Examples as long as the spirit of the present invention is not spoiled. The error bars in the graphs represent standard errors for three or more replicates of independent experiments.

1. Experimental Examples Using Mouse Ovarian Tumor Cell Line OV2944

<Preparation of OV2944 Cell Line>

The OV2944-HM-1 cell line (which may be referred to as "OV2944 cells" or, simply, "cells"), which is a commonly used cell line, was used. OV2944 cells were obtained from RIKEN BioResource Center (Cell No. RCB1483), and cultured in DMEM medium (+10% FBS) according to a conventional method. This line is a mouse ovarian cancer cell line, and shows a high lymph node metastatic ability.

Experiment Using Mouse Dicalcin (Preparation of Mouse Dicalcin)

Mouse dicalcin was prepared as follows. From mouse ovaries, total RNA was obtained using an RNA extraction reagent RNA-Bee (registered trademark) (AMS Biotech), and cDNA was prepared therefrom, followed by performing RT-PCR using a primer set corresponding to N- and C-terminal sequences of mouse dicalcin (Accession No.: NP_058020), to amplify the coding region of mouse dicalcin. As the primers, 5'-ATGCCTACAGAGACT-3' (SEQ ID NO:9) and 5'-TTAGATTCGCTTCTG-3' (SEQ ID NO:10) were used. The amplified PCR fragment was ligated into pGEM-T vector (Promega), and then subcloned into an expression vector pET17b (Novagen). The prepared vector was introduced into the *E. coli* pLysS strain (Novagen), and a recombinant protein was expressed in the *E. coli*, followed by purification of the protein by chromatography using a phenyl sepharose column and a DEAE column (GE Healthcare). The amino acid sequence of the prepared mouse dicalcin (full length) is represented by SEQ ID NO:11.

Cell Binding Experiment

Experimental Example 1-1

Cultured cells were fixed on a glass plate (4% paraformaldehyde/phosphate buffer, room temperature, 10 minutes), and treated with sheep serum. Thereafter, mouse dicalcin (5 μM) fluorescently labeled with tetramethylrhodamine (TMR) was reacted with the cells in the presence of 1 mM $CaCl_2$ (4° C., overnight). After washing with TBS buffer, analysis was carried out using a confocal microscope (Carl Zeiss). Further, cell nuclei were stained with DAPI. The results are shown in FIG. 1-1.

Experimental Example 1-2

Figures 1, 2:
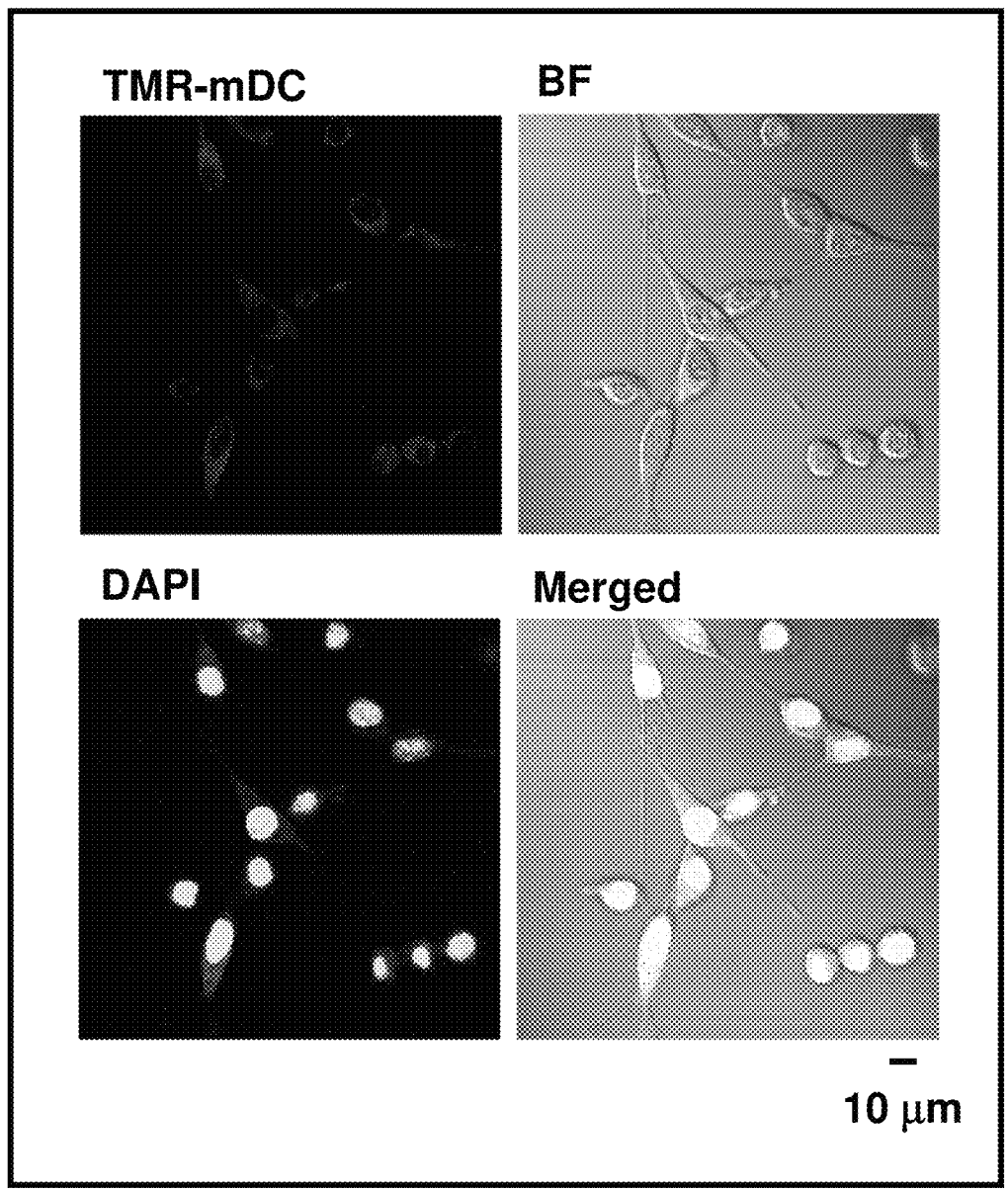

An experiment was carried out in the same manner as in Experimental Example 1-1 except that the reaction was carried out in the presence of 1 mM EGTA (which may be referred to as "in the absence of calcium"). The results are shown in FIG. 1-2.

Experimental Example 1-3

Figures 1, 2, 3:
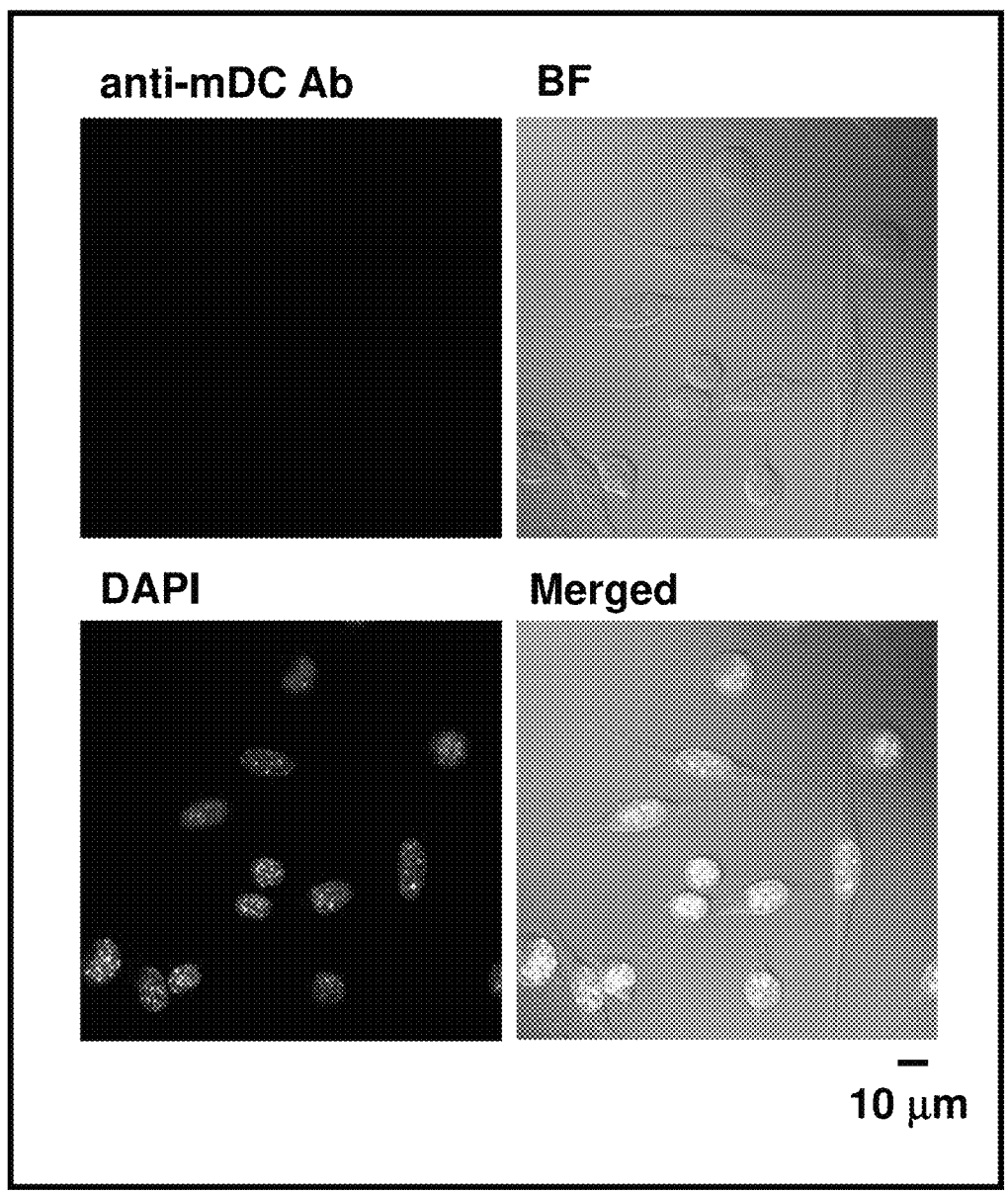
Figure 2:
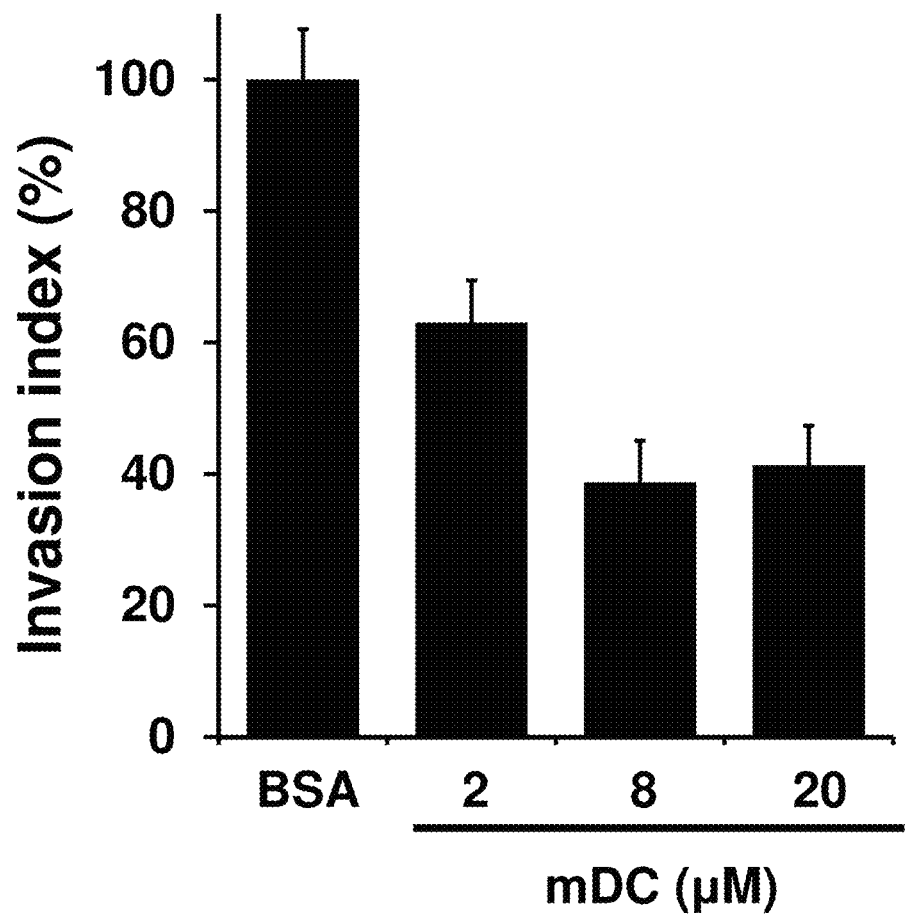
Figure 3:
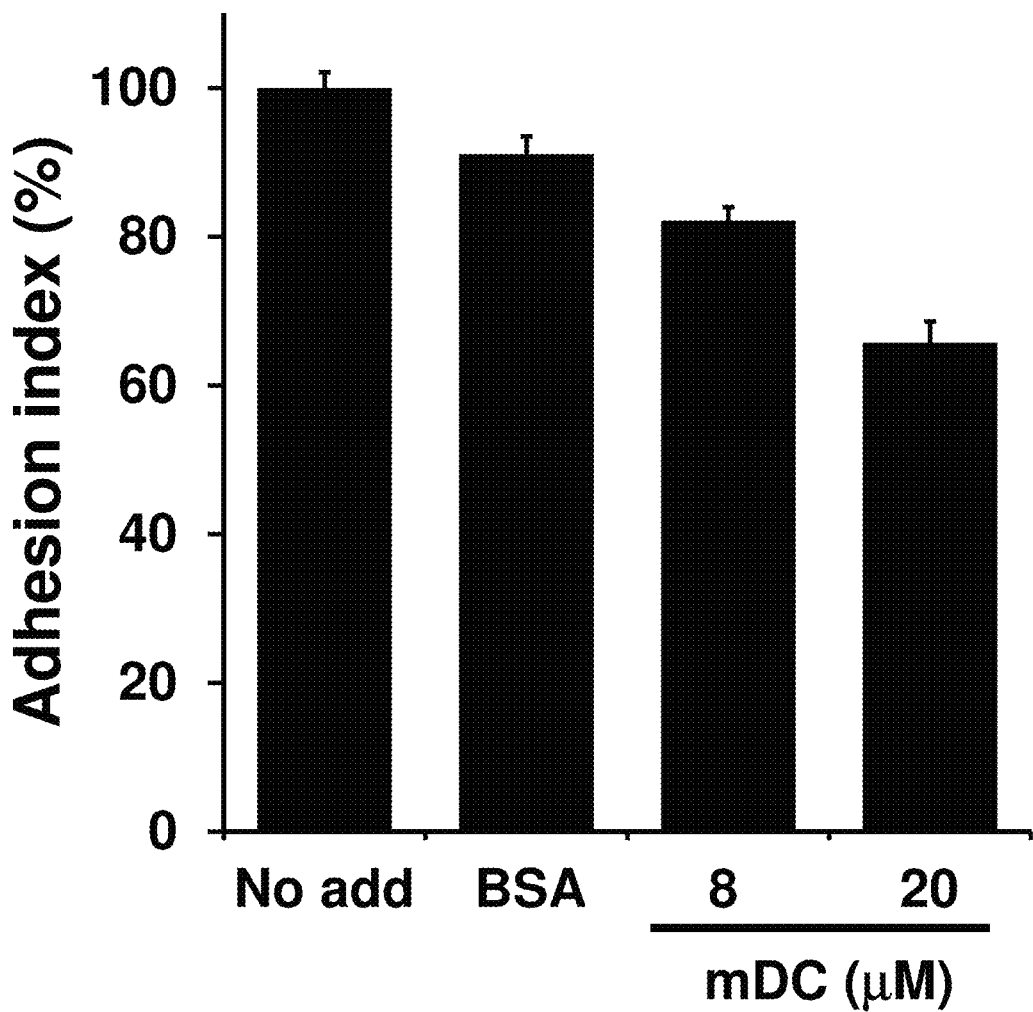

An experiment was carried out in the same manner as in Experimental Example 1-1 except that immunostaining was carried out using an anti-mouse dicalcin antibody (Catalog No. MAB5167, R&D Systems) as a primary antibody, and an Alexa Fluor (registered trademark) 594-labeled anti-rat IgG antibody (Catalog No. A11007, Invitrogen) as a secondary antibody. The results are shown in FIG. 1-3.

[Results]

According to FIG. 1-1 and FIG. 1-2, it was found that a larger amount of mouse dicalcin binds to the cells in the presence of calcium (1 mM $CaCl_2$)) than in the absence of calcium (1 mM EGTA). Further, according to FIG. 1-3, it was found that there is no endogenous dicalcin in the cells, and therefore that the fluorescences in FIG. 1-1 and FIG. 1-2 indicate binding of the dicalcin added, to the cells.

Cell Invasion Assay

Experimental Example 2-1

Cell invasion was analyzed using a BD BioCoat (registered trademark) Matrigel Invasion Chamber (Becton, Dickinson and Company). First, a certain amount of cells (about $1 \times 10^5$ cells/well) were treated with 2 μM, 8 μM, or 20 μM mouse dicalcin at room temperature for 20 minutes.

The treated cells were washed by centrifugation treatment, and then plated in the upper chamber of a transwell preliminarily coated with Matrigel, followed by performing culture using DMEM (+10% FBS) as a medium.

About 16 hours later, the invading cells that had migrated into the lower chamber were fixed using 4% paraformaldehyde/phosphate buffer at room temperature for 10 minutes, and then stained with crystal violet, followed by excision of the membrane, embedding on a slide, and counting of the cell number. The invasion index was calculated as {(number of stained cells)/(number of plated cells)}×100(%), and normalized by the later-mentioned result of Experimental Example 2-2, which was taken as 100(%).

Experimental Example 2-2

An experiment was carried out in the same manner as in Experimental Example 2-1 except that 10 µM BSA was used instead of mouse dicalcin.
[Results]
The results are shown in FIG. 2. It was found that mouse dicalcin suppresses the cell invasion in a concentration-dependent manner.

Cell Adhesion Assay

Experimental Example 3-1

First, a certain amount of cells (about 1×10$^5$ cells/well) were treated with 8 µM or 20 µM mouse dicalcin at room temperature for 20 minutes. After coating a 24-well plate with, and allowing gelation of, BD Matrigel (registered trademark) (Becton, Dickinson and Company), the pretreated cells were washed and plated therein.

About 1 hour later, nonadherent cells were aspirated. After washing, adherent cells were fixed using 4% paraformaldehyde/phosphate buffer at room temperature for 10 minutes, and then stained with crystal violet, followed by counting of the cell number. The adhesion index was calculated as {(number of stained cells)/(number of plated cells)}×100(%). Normalization was carried out by the later-mentioned result of Experimental Example 3-2, which was taken as 100(%).

Experimental Example 3-2

An experiment was carried out in the same manner as in Experimental Example 3-1 except that mouse dicalcin was not added.

Experimental Example 3-3

An experiment was carried out in the same manner as in Experimental Example 3-1 except that 10 µM BSA was used instead of mouse dicalcin.
[Results]
The results are shown in FIG. 3. It was found that mouse dicalcin suppresses the cell adhesion in a concentration-dependent manner.

Cell Survival Assay

Experimental Example 4-1

First, a certain amount of cells (about 1×10$^5$ cells/well) were treated with 20 µM mouse dicalcin at room temperature for 20 minutes. The cells were then washed and aliquoted into a 96-well plate, followed by performing culture. One hour later, after washing with PBS buffer, the cells were fixed using 4% paraformaldehyde/phosphate buffer at room temperature for 10 minutes. The cells were then stained with crystal violet and solubilized, followed by measuring the absorbance (measurement wavelength, 550 nm) in order to analyze the cell survival rate. The cell survival rate was calculated as {(number of stained cells)/(number of plated cells)}×100(%). Normalization was carried out by the later-mentioned result of Experimental Example 4-2, which was taken as 100(%).

Experimental Example 4-2

Figure 4:
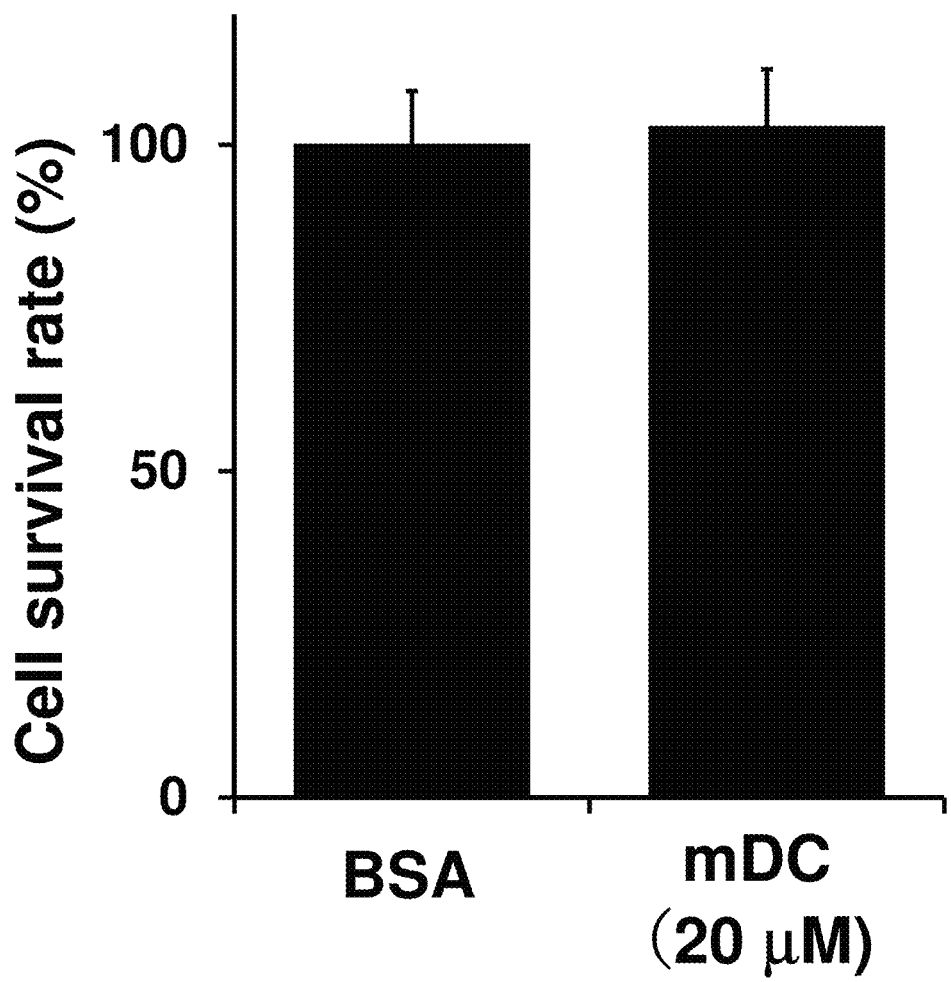
FIG. 4 shows a graph illustrating the results of a cell survival assay in one experimental example in the present invention.

An experiment was carried out in the same manner as in Experimental Example 4-1 except that 10 µM BSA was used instead of mouse dicalcin.
[Results]
The results are shown in FIG. 4. It was found that treatment of the cells with mouse dicalcin does not affect the survival of the cells.

Figures 1, 5:
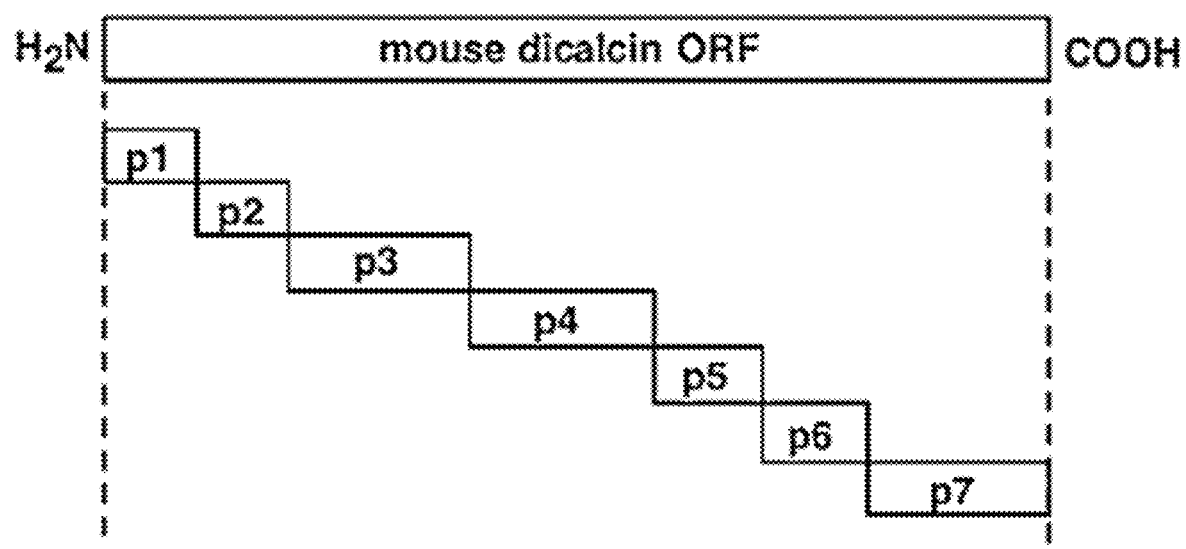
Figures 2, 5:
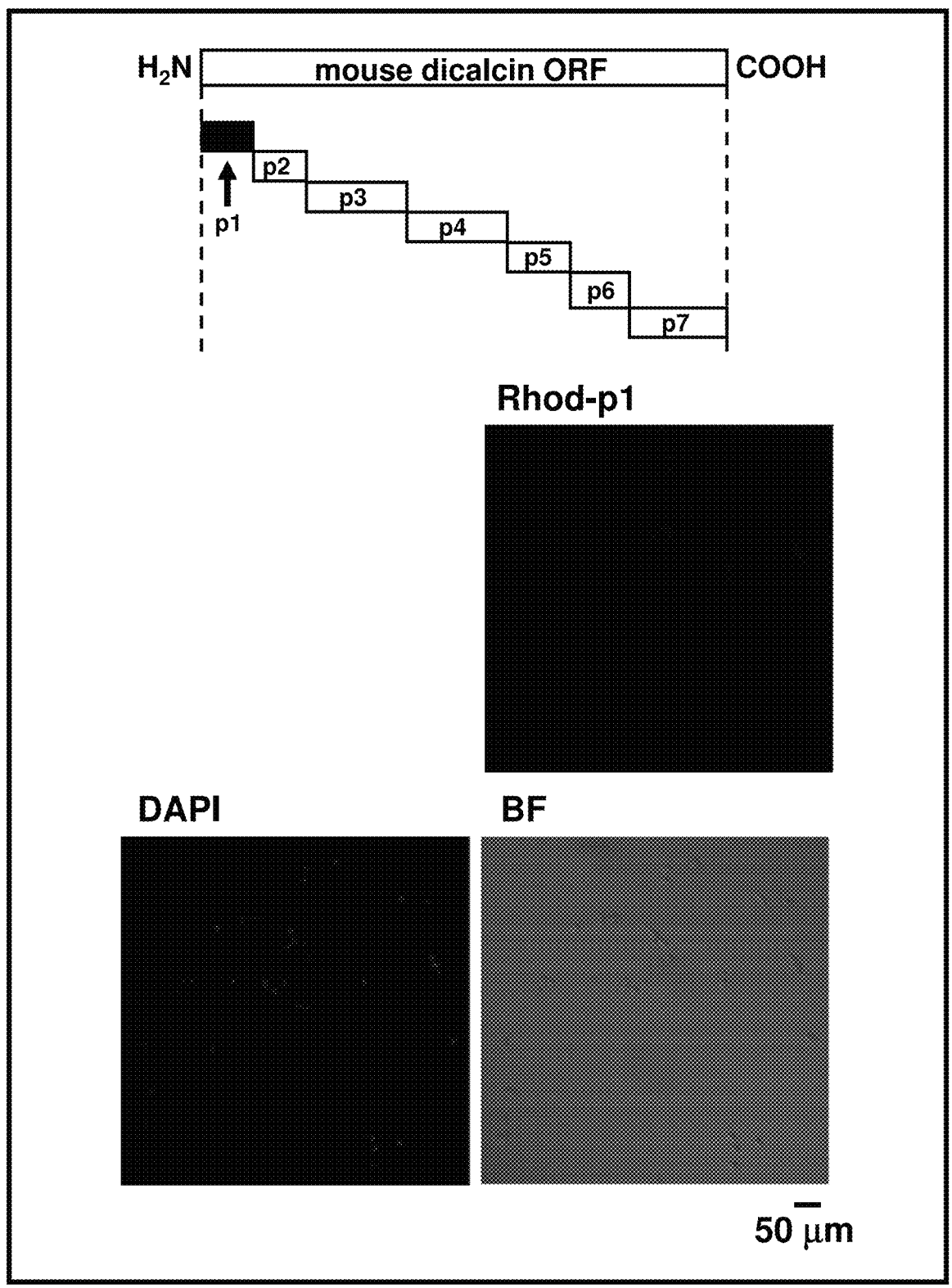
Figures 3, 5:
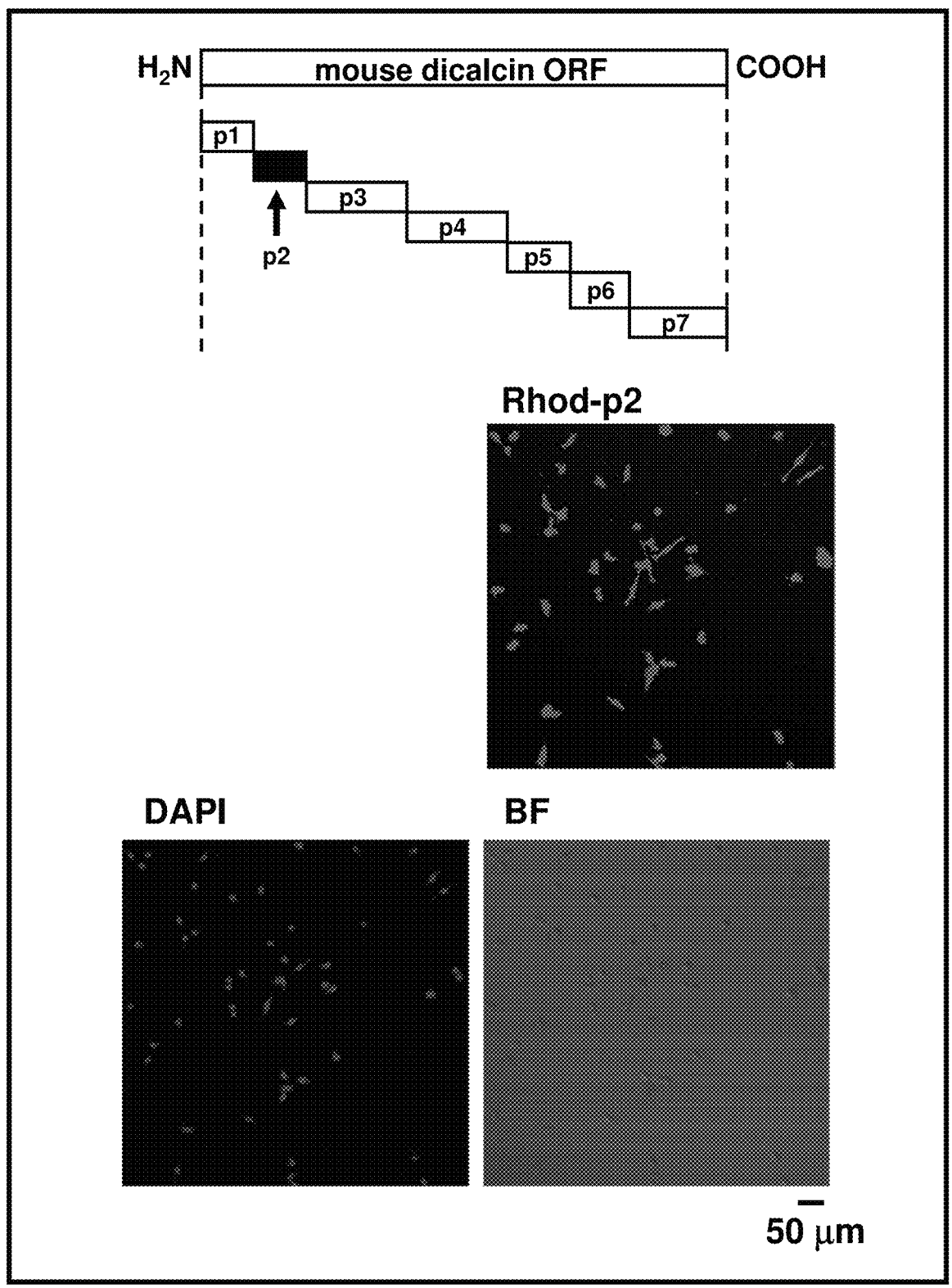
Figures 4, 5:
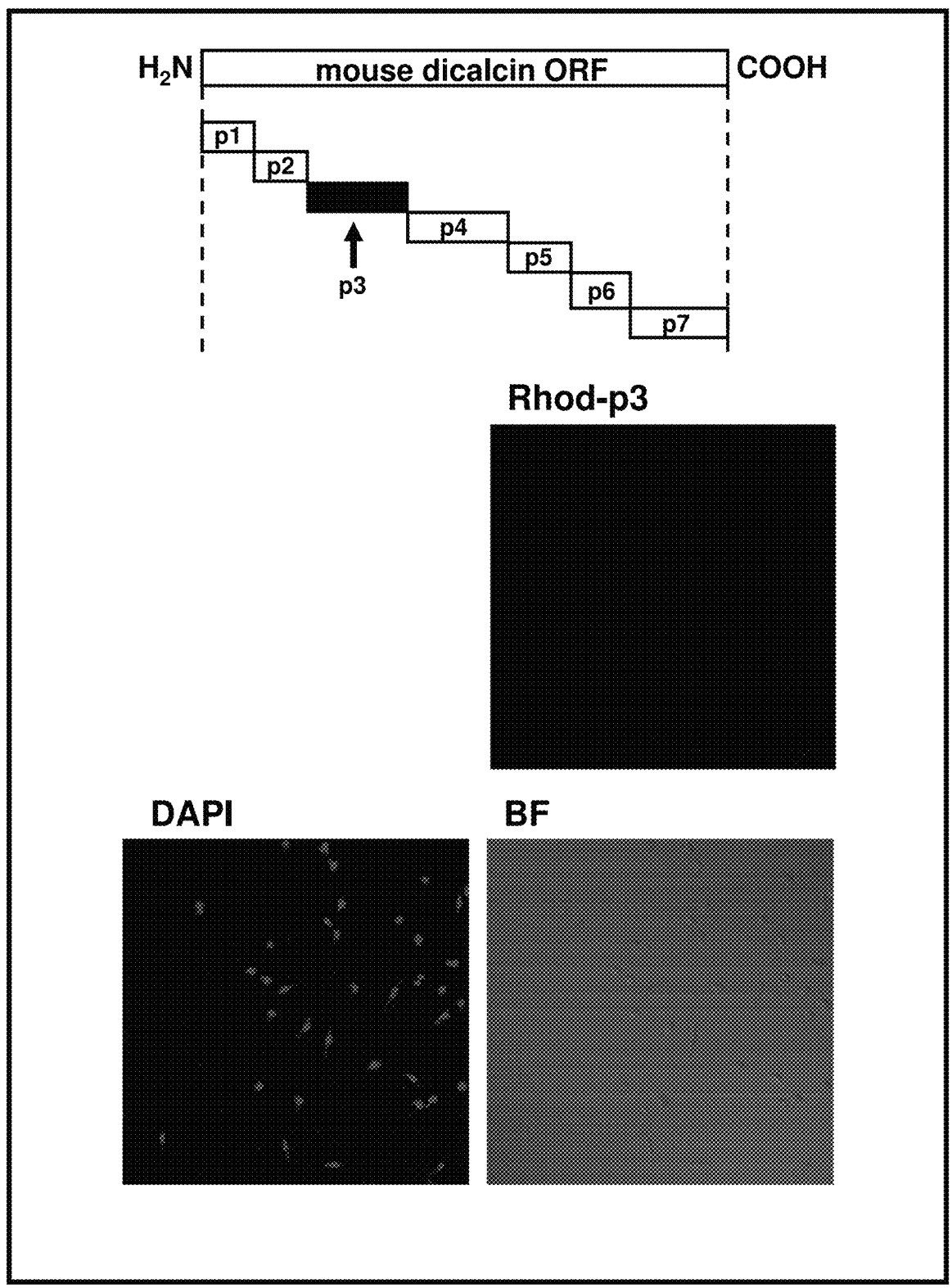
Figure 5:
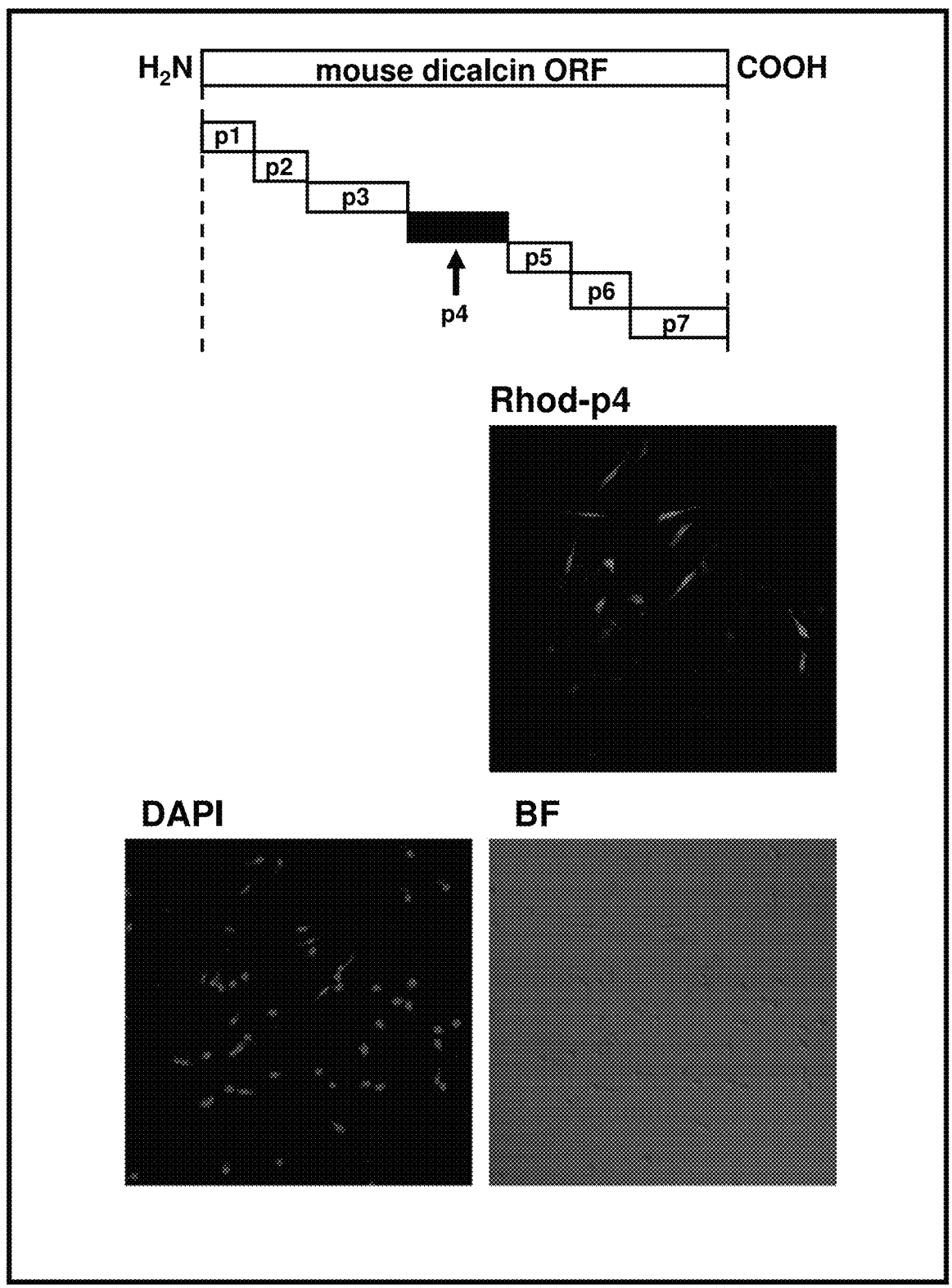

Experiment Using Partial Peptides of Mouse Dicalcin (Synthesis of Partial Peptides of Mouse Dicalcin)
Partial peptides p1 to p7 of mouse dicalcin were synthesized. Each amino acid sequence is as follows. The positions of partial peptides p1 to p7 along the full-length mouse dicalcin are as shown in FIG. 5-1.

p1:
PTETERCIE (SEQ ID NO: 12)

p2:
SLIAVFQKY (SEQ ID NO: 13)

p3:
SGKDGNNTQLSKTEFLSF (SEQ ID NO: 14)

p4:
MNTELAAFTKNQKDPGVLDR (SEQ ID NO: 15)

p5:
MMKKLDLNCDG (SEQ ID NO: 16)

p6:
QLDFQEFLNLI (SEQ ID NO: 17)

p7:
GGLAIACHDSFIQTSQKRI (SEQ ID NO: 18)

Cell Binding Experiment

Experimental Example 5-1

An experiment was carried out in the same manner as in Experimental Example 1-1 except that each of partial peptides p1 to p7 (5 µM) fluorescently labeled with rhodamine was used. The results are shown in FIG. 5-2 to FIG. 5-8.

When partial peptide p6 was used, immunocytostaining was also carried out using an anti-CD44 antibody (Abcam) against CD44 as a plasma membrane molecule control, and an Alexa Fluor (registered trademark) 488-labeled anti-rat IgG antibody (Catalog No. A21208, Invitrogen) as a secondary antibody. The results, including a result of nuclear staining with Hoechst, are shown in FIG. 5-9.

[Results]

The fluorescence intensity is shown in FIG. 5-10. According to the fluorescence intensity, partial peptide p6 showed the highest cell-binding ability; p2, p5, and p7 showed the second highest cell-binding ability; and p4 showed the third highest cell-binding ability. It was also found that partial peptide p6 binds to the plasma membranes of cells (the arrowhead in FIG. 5-9).

Cell Invasion Assay

Experimental Example 6-1

An analysis was carried out in the same manner as in Experimental Example 2-1 using partial peptides p2, p5, p6, and p7 (8 µM each).

Experimental Example 6-2

Figures 5, 6:
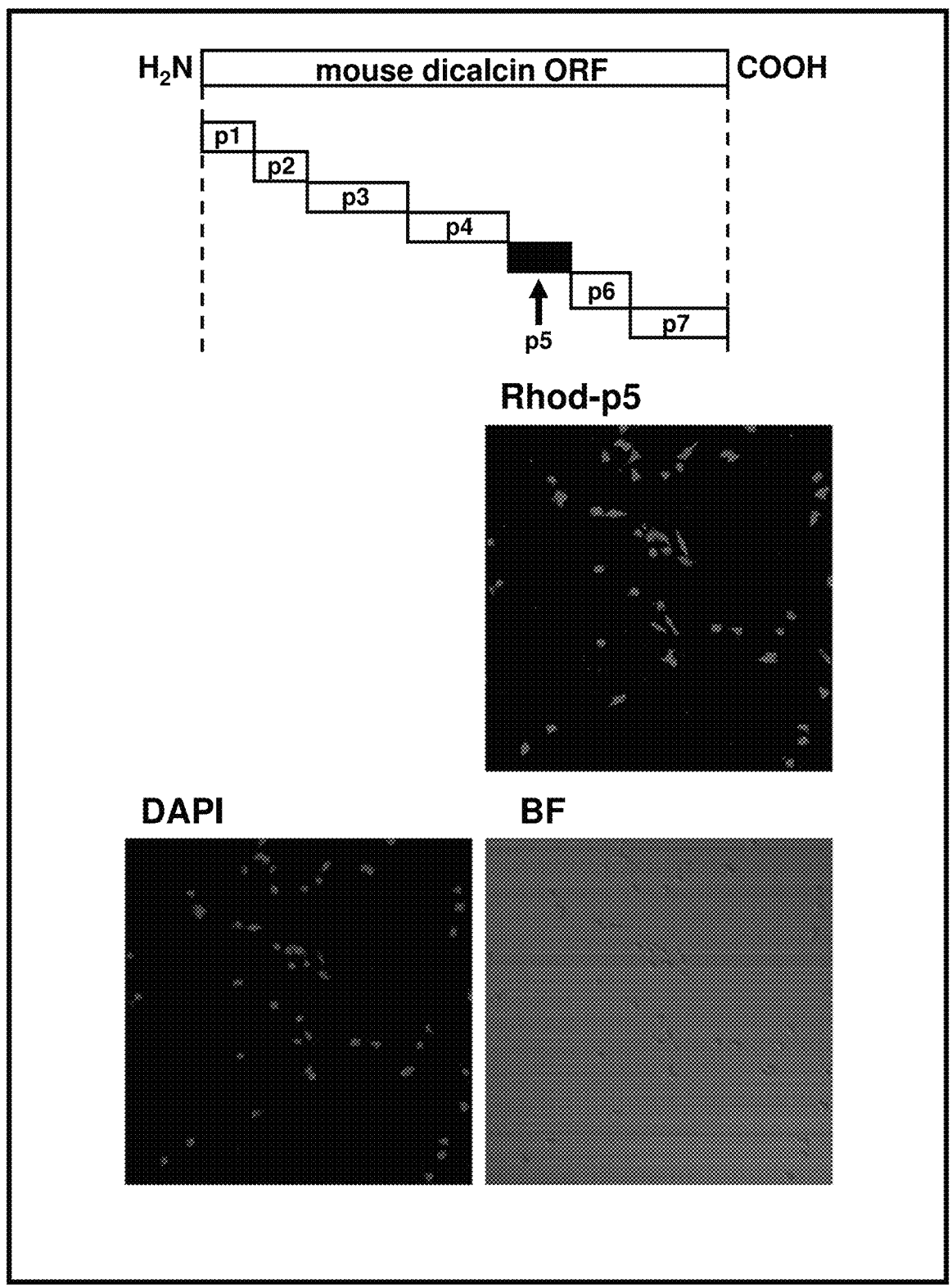

An analysis was carried out in the same manner as in Experimental Example 6-1 except that 10 µM BSA was used instead of the partial peptides.
[Results]
The results are shown in FIG. 6. It was found that partial peptide p6 suppresses cell invasion at the highest level, followed by p2, p'7, and p5 in this order.

Experimental Example 7

Figures 5, 6, 7:
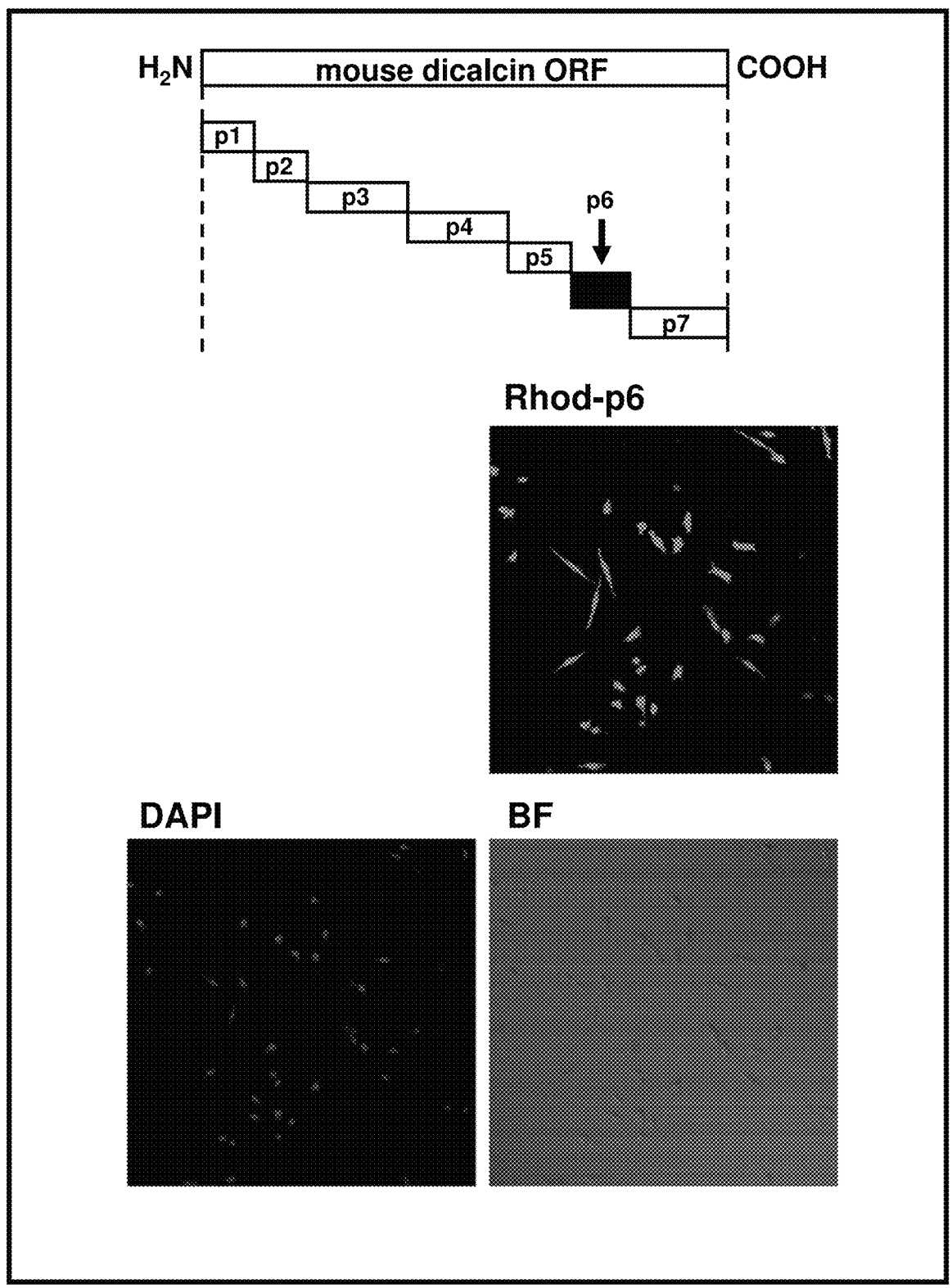

Using different concentrations of partial peptide p6, which suppresses cell invasion at the highest level, a cell invasion assay was carried out in order to determine the concentration of partial peptide p6 at which the invasion index becomes 50, that is, $IC_{50}$ (µM). The analysis was carried out in the same manner as in Experimental Example 6-1 using partial peptide p6 at concentrations of 0.2 µM, 0.8 µM, 2 µM, 8 µM, and 20 µM.
[Results]
The results are shown in FIG. 7. Partial peptide p6 suppressed cell invasion in a concentration-dependent manner, and $IC_{50}$ was 2 µM.

Cell Migration Assay

Experimental Example 8-1

The plasmid vector pDsRed2-C1 (Clontech), which expresses a fluorescent protein (DsRed2), was transfected into cells. The cells were plated on a glass plate, and observed under the microscope at 1-hour intervals in the presence of partial peptide p6 (5 µM) while measuring the displacement on a display. The observation was carried out for 12 to 37 cells. Statistical analysis was carried out by unpaired Student t-test in order to analyze a significant difference.

Experimental Example 8-2

An experiment was carried out in the same manner as in Experimental Example 8-1 except that partial peptide p1 (5 µM) was used instead of partial peptide p6.

Experimental Example 8-3

An experiment was carried out in the same manner as in Experimental Example 8-1 except that no partial peptide was added.

[Results]
FIG. 8A shows images of the cells after the transfection, and FIG. 8B shows the results of the assays. It was found that partial peptide p6 suppresses migration of the cells.

2. Experimental Examples Using Human Ovarian Tumor Cell Line OVCAR

<Preparation of OVCAR Cell Line>
The OVCAR-3 cell line (which may be referred to as "OVCAR cells" or, simply, "cells"), which is a commonly used cell line, was used. OVCAR cells were obtained from RIKEN BioResource Center (Cell No. RCB2135), and cultured in DMEM medium (+10% FBS) according to a conventional method. This line is a human ovarian cancer (adenocarcinoma)-derived cell line.
<Experiment Using Human Dicalcin>
(Preparation of Human Dicalcin)
cDNA of human dicalcin was obtained from Kazusa DNA Research Institute (clone No.: pF1KB6753, Accession No.: AB464185). RT-PCR was carried out using a primer set corresponding to N- and C-terminal sequences of human dicalcin, to amplify the coding region of human dicalcin. As the primers, 5'-ATGGCAAAAATCTCCAGCCCTA-3' (SEQ ID NO:19) and 5'-TTAGGTCCGCTTCTGGGAAG-3' (SEQ ID NO:20) were used. Thereafter, human dicalcin (full length) was prepared in the same manner as described in the "Preparation of Mouse Dicalcin" section. The amino acid sequence of the prepared human dicalcin (full length) is the amino acid sequence represented by SEQ ID NO:1.

Cell Invasion Assay

Experimental Example 9-1

An analysis was carried out in the same manner as in Experimental Example 2-1 except that OVCAR cells were used as the cells, and that 8 µM or 20 µM human dicalcin was used instead of mouse dicalcin.

Experimental Example 9-2

Figures 5, 6, 7, 8:
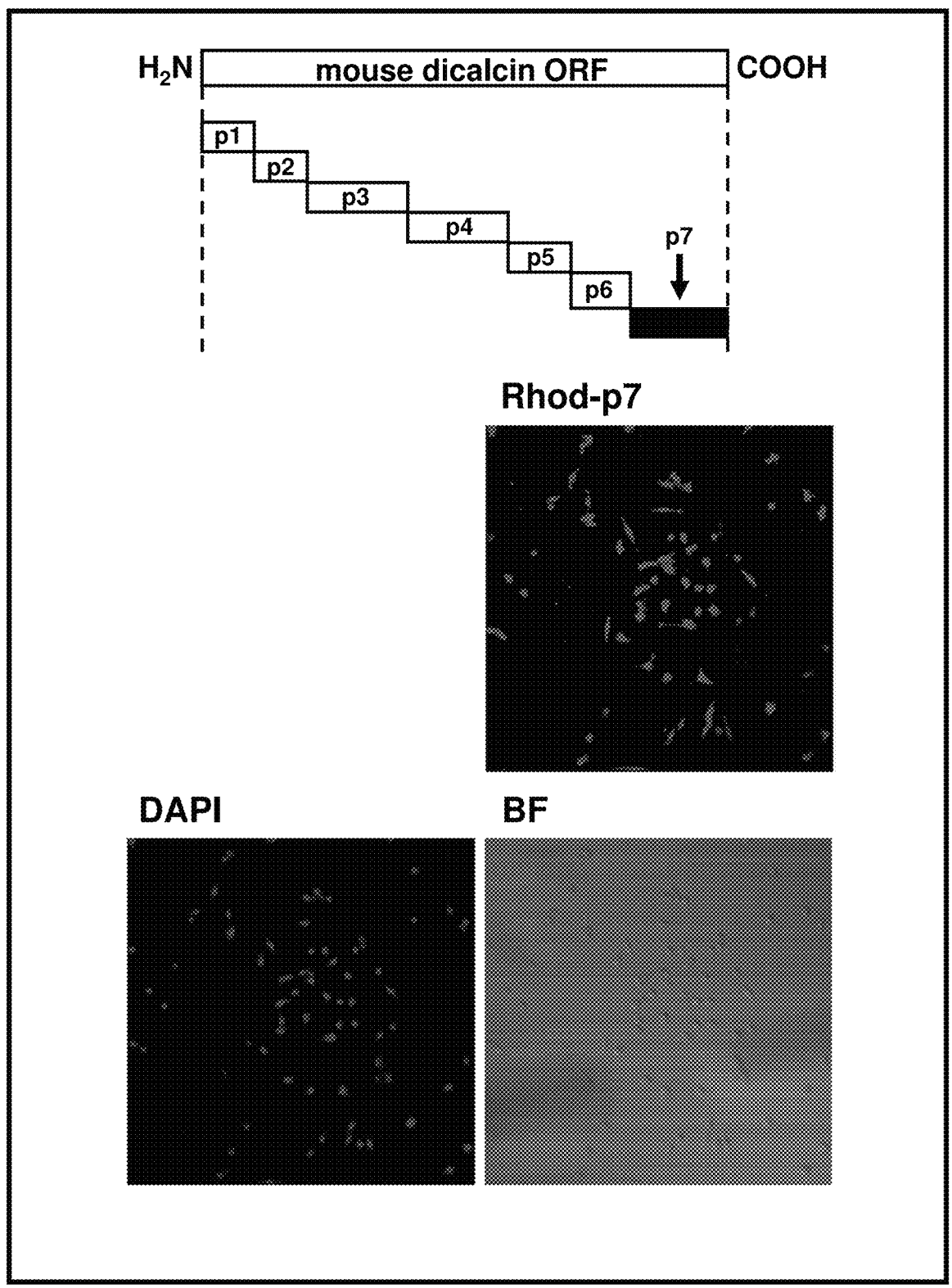
Figures 5, 6, 7, 8, 9:
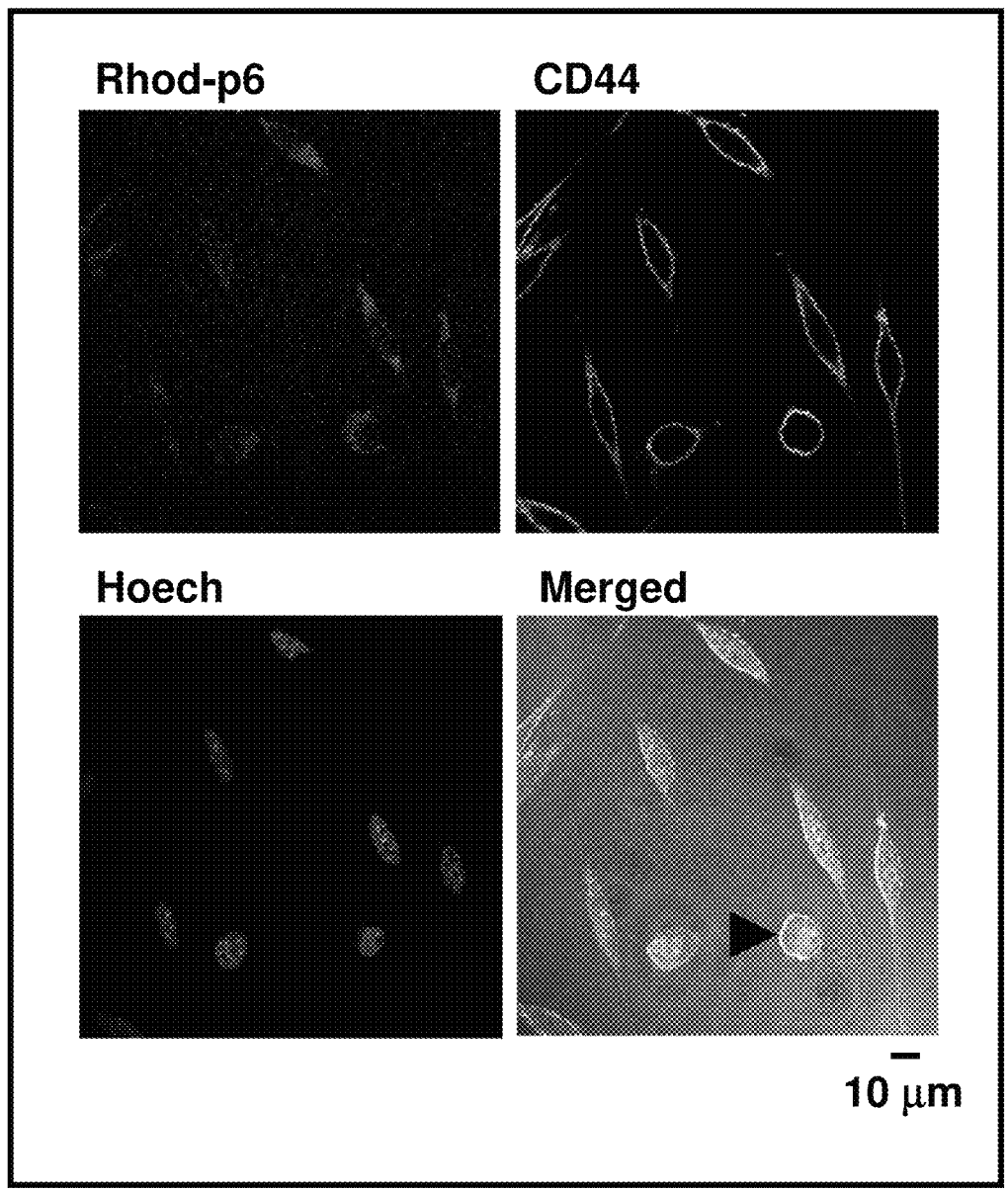
Figure 6:
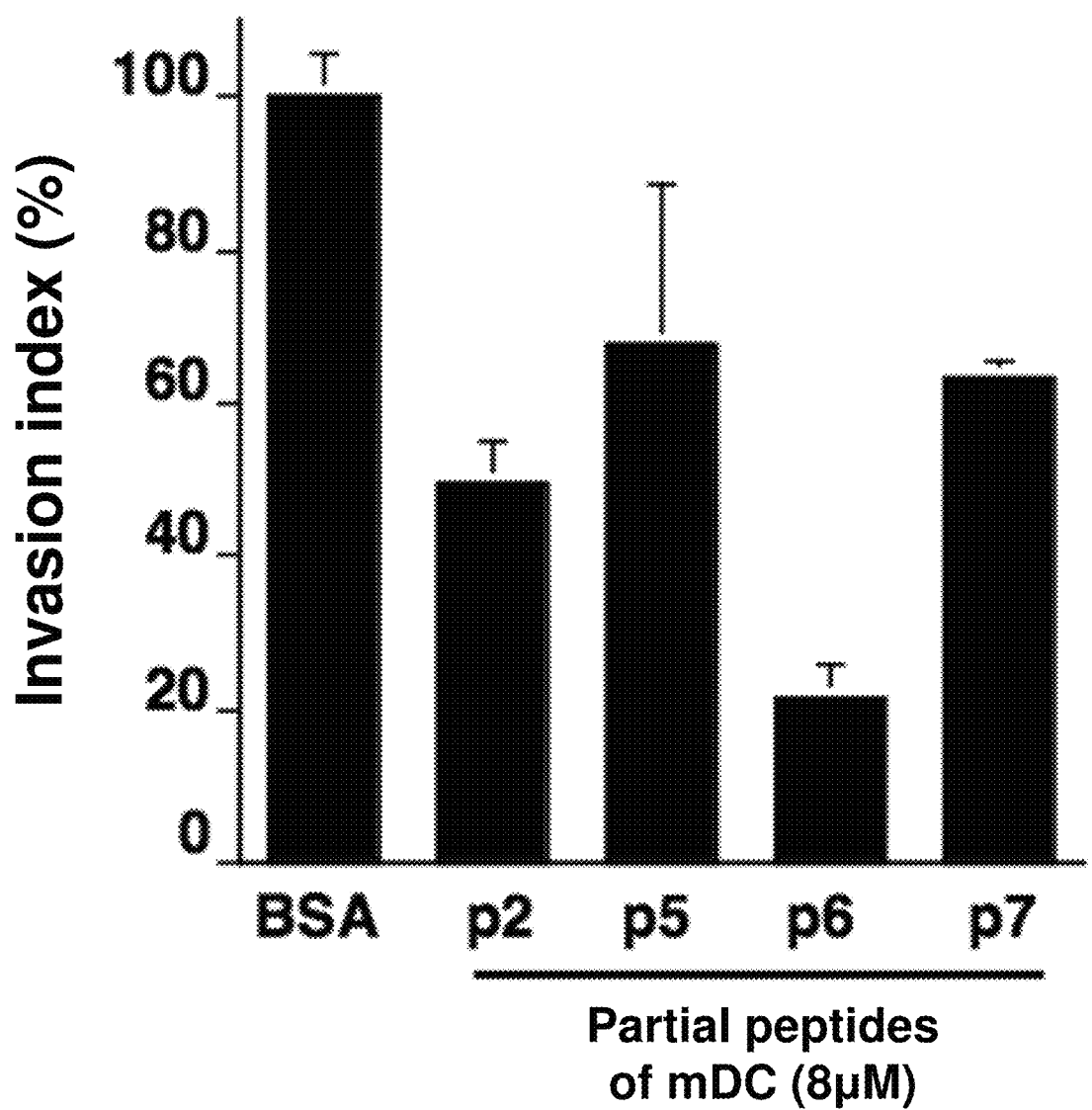
Figure 7:
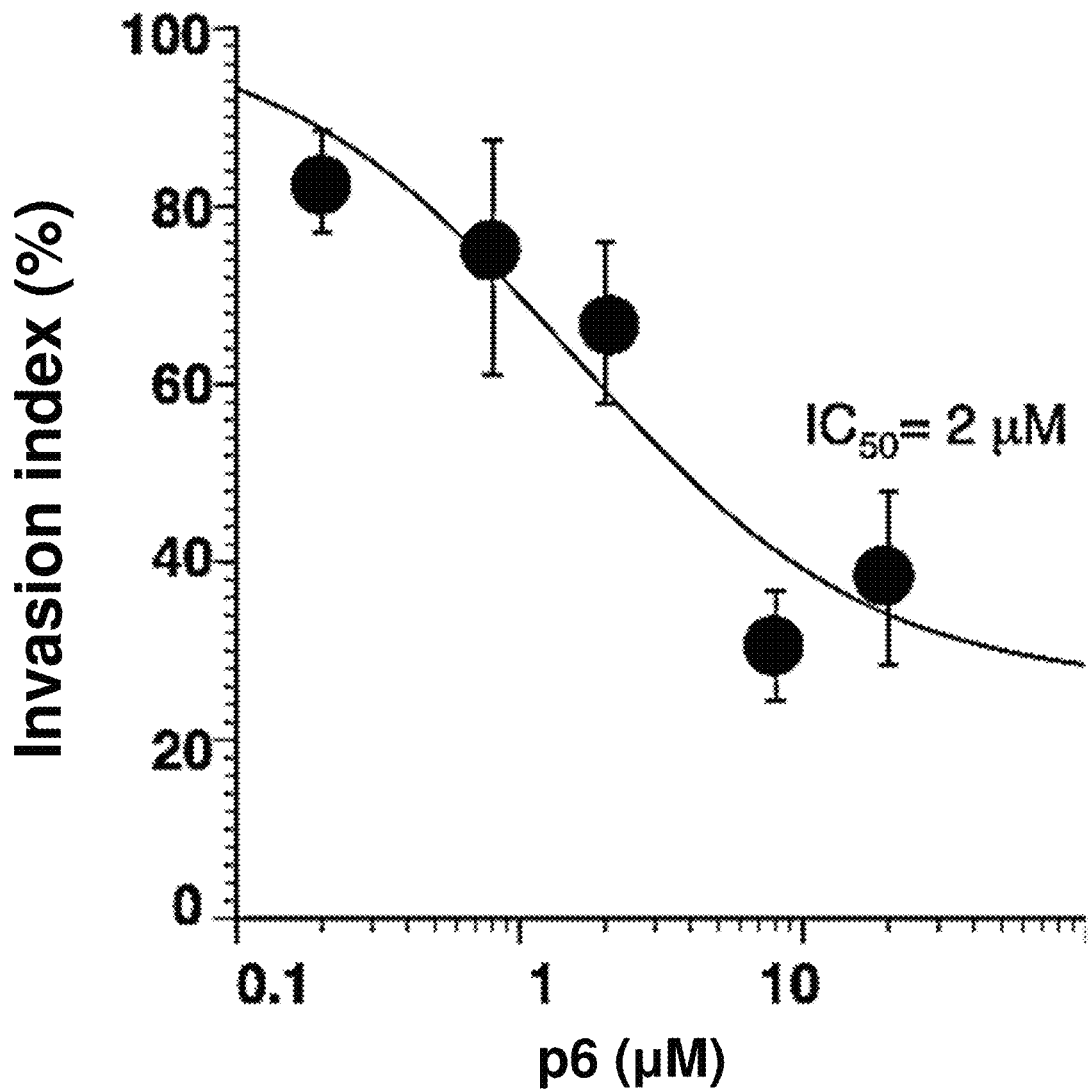
Figure 9:
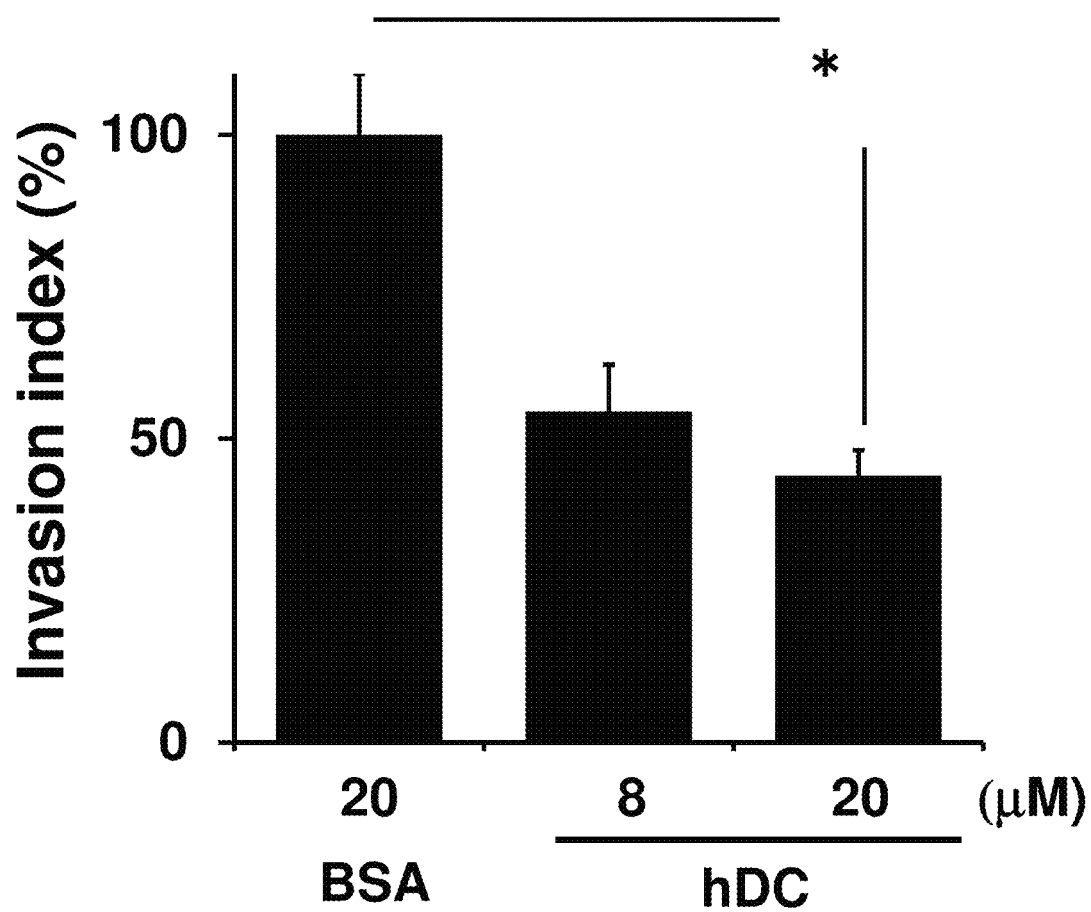

An analysis was carried out in the same manner as in Experimental Example 9-1 except that 20 µM BSA was used instead of human dicalcin.
[Results]
The results are shown in FIG. 9. It was found that human dicalcin suppresses the cell invasion in a concentration-dependent manner. When human dicalcin (20 µM) was used, the invasion index was 43.9%.

Cell Survival Assay

Experimental Example 10-1

An experiment was carried out in the same manner as in Experimental Example 4-1 except that OVCAR cells were used as the cells, and that 20 µM human dicalcin was used instead of mouse dicalcin.

Experimental Example 10-2

An experiment was carried out in the same manner as in Experimental Example 10-1 except that 10 µM BSA was used instead of human dicalcin.

[Results]

Figure 10:
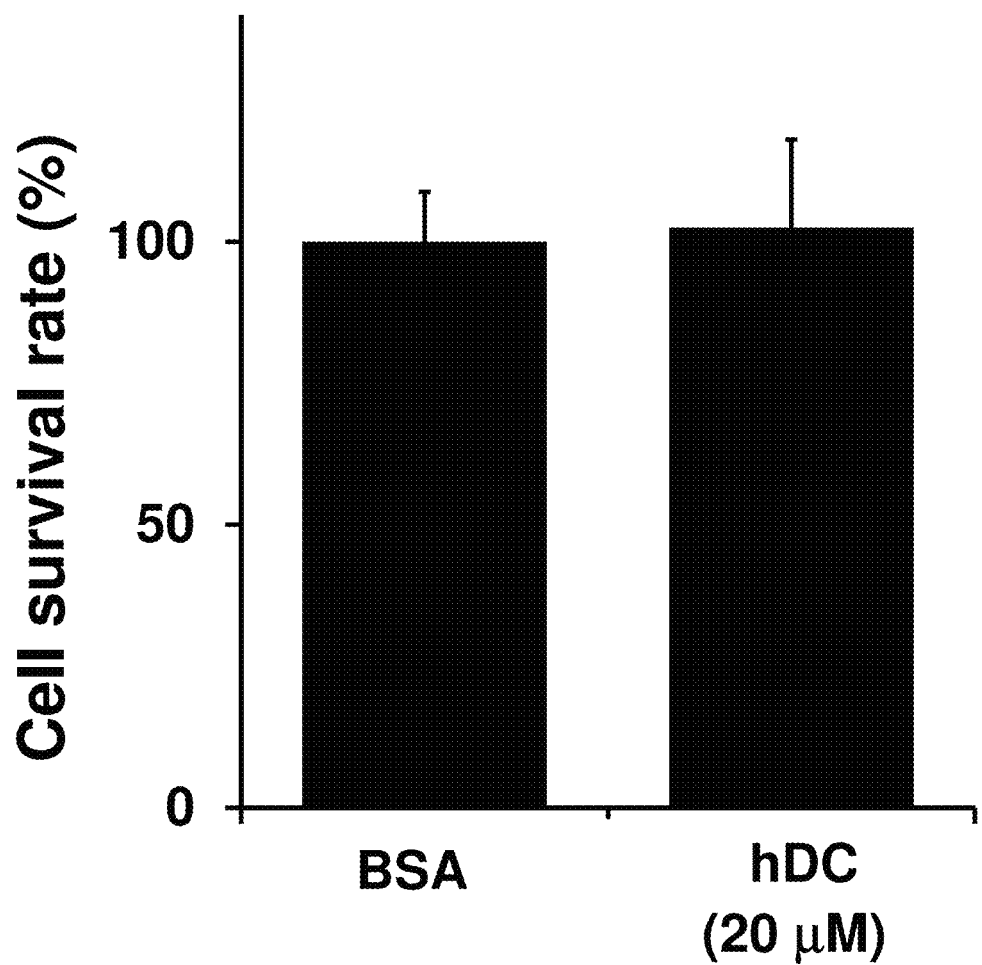

The results are shown in FIG. 10. It was found that treatment of the cells with human dicalcin does not affect the survival of the cells.

<Experiment Using Partial Peptides of Human Dicalcin>
(Synthesis of Partial Peptides of Human Dicalcin)

Partial peptides hDC-p1 to hDC-p7 of human dicalcin (which correspond to partial peptides p1 to p7 of mouse dicalcin, respectively) were synthesized. Each amino acid sequence is as follows.

```
hDC-p1:
                                    (SEQ ID NO: 2)
PTETERCIE hDC-p2:
                                    (SEQ ID NO: 3)
SLIAVFQKY hDC-p3:
                                    (SEQ ID NO: 4)
AGKDGYNYTLSKTEFLSF hDC-p4:
                                    (SEQ ID NO: 5)
MNTELAAFTKNQKDPGVLDR hDC-p5:
                                    (SEQ ID NO: 6)
MMKKLDTNSDG hDC-p6:
                                    (SEQ ID NO: 7)
QLDFSEFLNLI hDC-p7:
                                    (SEQ ID NO: 8)
GGLAMACHDSFLKAVPSQKRT
```

Cell Binding Experiment

Experimental Example 11-1

Figures 1, 11:
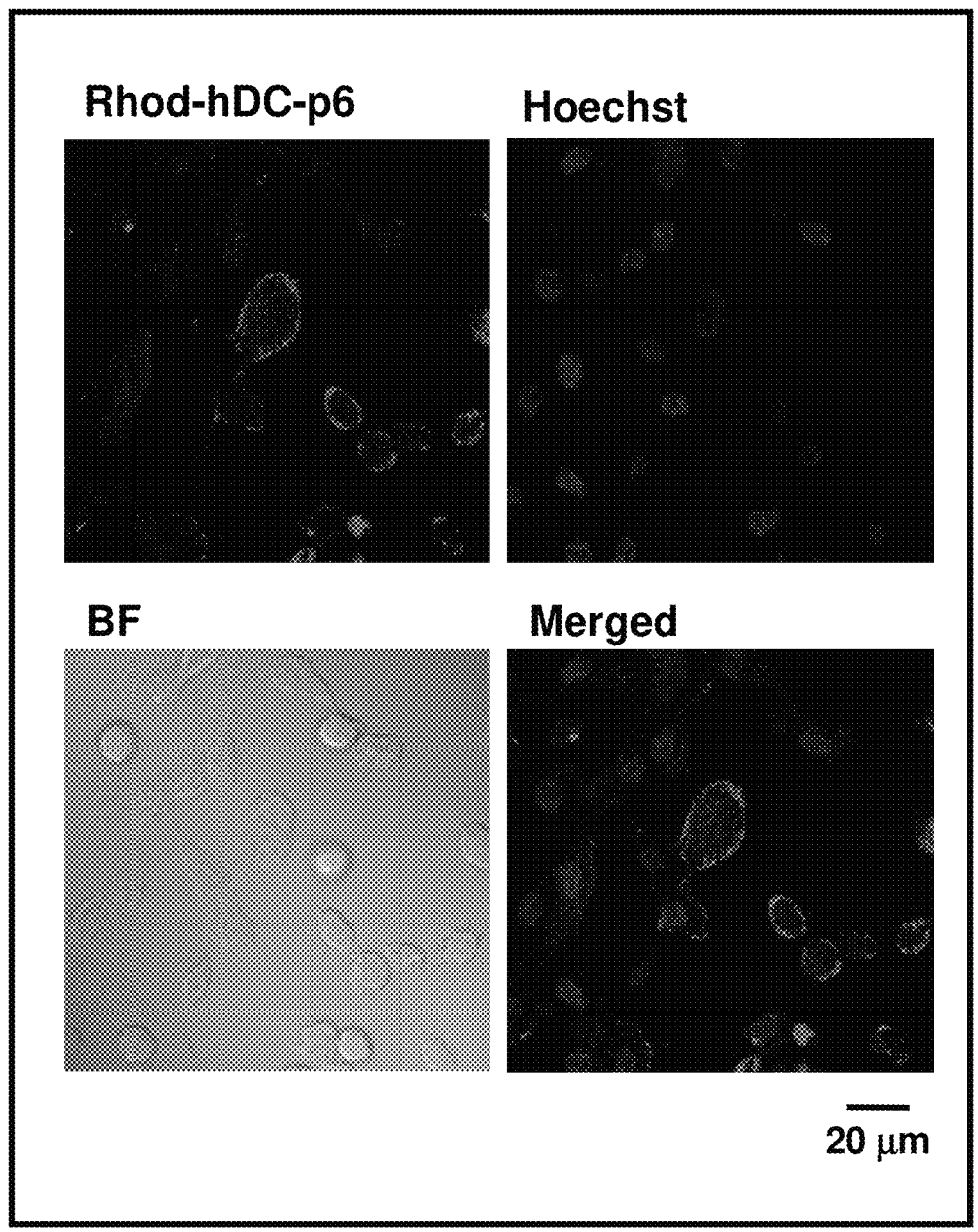
Figures 2, 11:
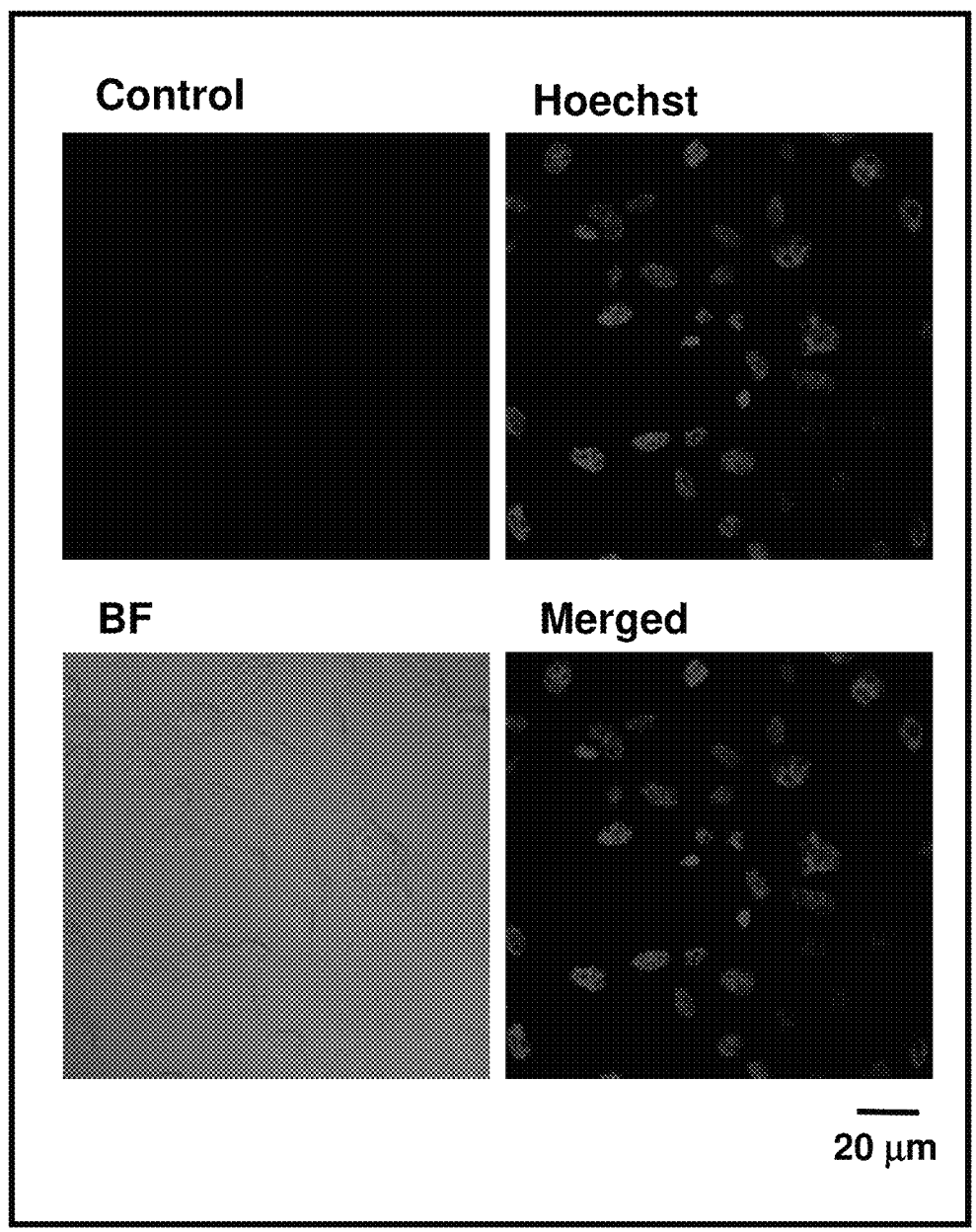

An experiment was carried out in the same manner as in Experimental Example 5-1 except that OVCAR cells were used as the cells, that partial peptide hDC-p6 (5 µM) fluorescently labeled with rhodamine was used, that calcium was absent, and that Hoechst was used for nuclear staining. The results are shown in FIG. 11-1.

Experimental Example 11-2

An experiment was carried out in the same manner as in Experimental Example 11-1 except that partial peptide p1 (5 µM) was used as a control peptide, instead of partial peptide hDC-p6. The results are shown in FIG. 11-2.
[Results]

According to the fluorescence intensity, it was found that partial peptide hDC-p6 binds to the cells.

Cell Invasion Assay

Experimental Example 12-1

An analysis was carried out in the same manner as in Experimental Example 2-1 except that OVCAR cells were used as the cells, and that 2 µM or 10 µM hDC-p6 was used as a partial peptide. Statistical analysis was carried out by unpaired Student t-test in order to analyze a significant difference.

Experimental Example 12-2

An analysis was carried out in the same manner as in Experimental Example 12-1 except that partial peptide p1 (10 µM) was used as a control peptide, instead of partial peptide hDC-p6.
[Results]

Figures 1, 12:
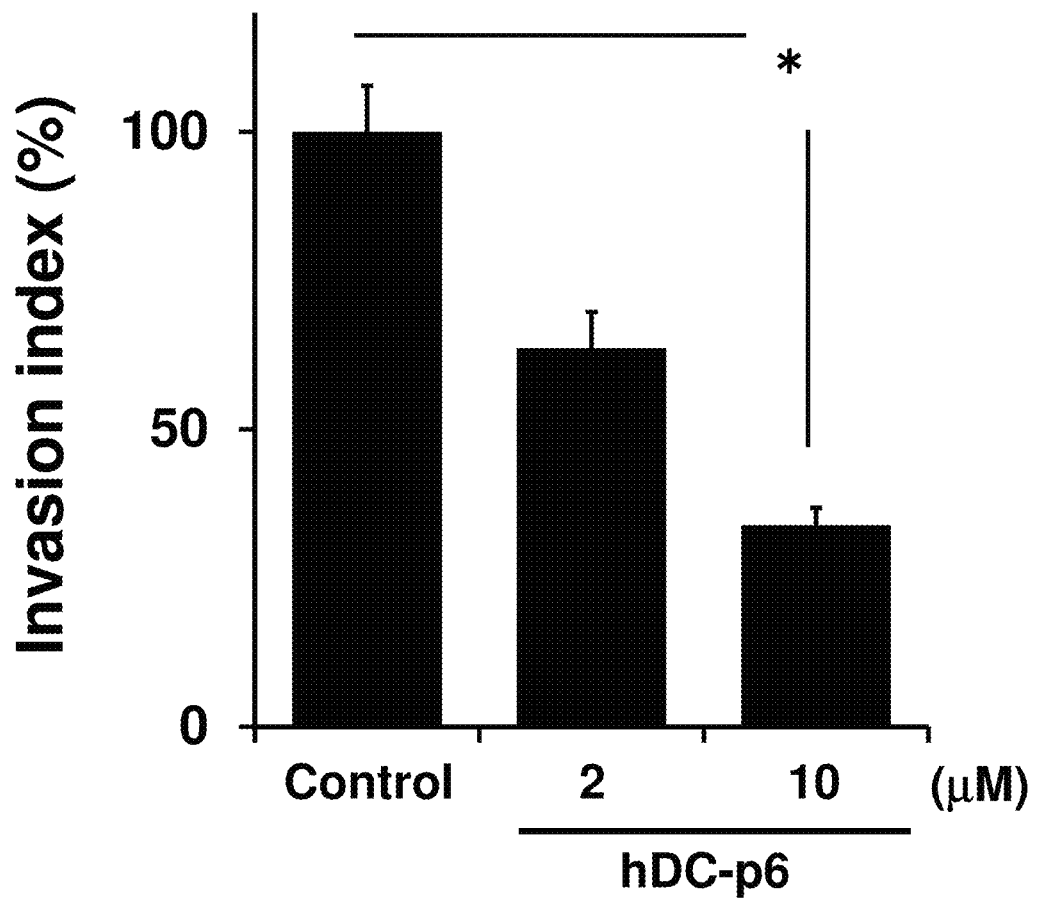
Figures 2, 12:
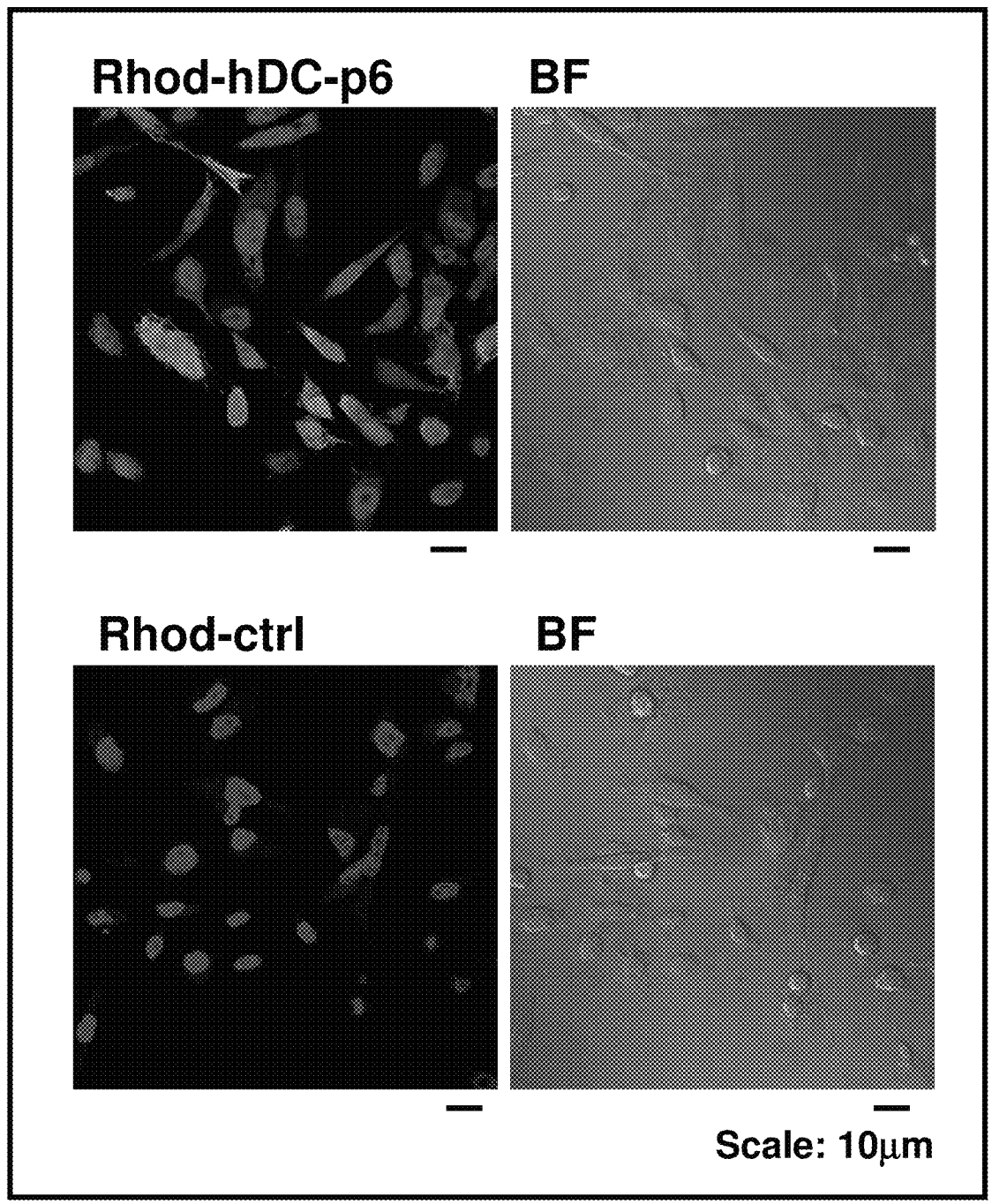
Figures 3, 12:
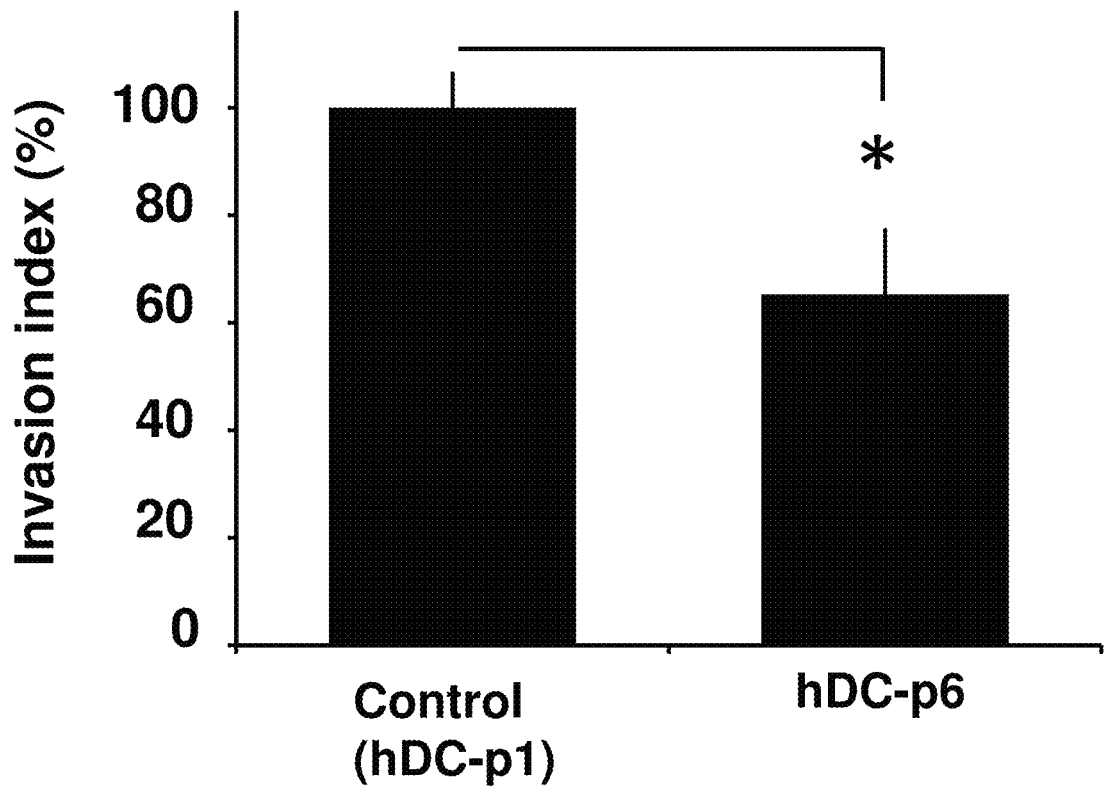

The results are shown in FIG. 12-1. It was found that partial peptide hDC-p6 suppresses cell invasion in a concentration-dependent manner.

3. Experimental Examples Using Human Prostate Cancer Cell Line PC-3

<Preparation of PC-3 Cell Line>

The PC-3 cell line (which may be referred to as "PC-3 cells" or, simply, "cells"), which is a commonly used cell line, was used. PC-3 cells were obtained from RIKEN BioResource Center (Cell No. RCB2145), and cultured in DMEM medium (+10% FBS) according to a conventional method. This line is a human prostate cancer-derived cell line.

Experiment Using Partial Peptides of Human Dicalcin

Cell Binding Experiment

Experimental Example 12-3

An experiment was carried out in the same manner as in Experimental Example 5-1 except that PC-3 cells were used as the cells, that partial peptide hDC-p6 (5 µM) fluorescently labeled with rhodamine was used, that calcium was absent, and that Hoechst was used for nuclear staining.

Experimental Example 12-4

An experiment was carried out in the same manner as in Experimental Example 12-3 except that partial peptide hDC-p1 (5 µM) was used as a control peptide, instead of partial peptide hDC-p6.
[Results]

The results are shown in FIG. 12-2. According to the fluorescence intensity, it was found that partial peptide hDC-p6 binds to the cells.

Cell Invasion Assay

Experimental Example 12-5

An analysis was carried out in the same manner as in Experimental Example 2-1 except that PC-3 cells were used as the cells, and that 10 µM hDC-p6 was used as a partial peptide. Statistical analysis was carried out by unpaired Student t-test in order to analyze a significant difference.

Experimental Example 12-6

An analysis was carried out in the same manner as in Experimental Example 12-5 except that partial peptide hDC-p1 (10 µM) was used as a control peptide, instead of partial peptide hDC-p6.
[Results]

The results are shown in FIG. 12-3. It was found that partial peptide hDC-p6 suppresses cell invasion.

4. Metastasis Inhibition Assay Using Mouse Ovarian Tumor Cell Line OV2944

(Preparation of OV2944 Cells Expressing Fluorescent Protein tdTomato)

The plasmid vector ptdTomato-C1 (Clontech), which expresses the fluorescent protein tdTomato, was transfected into OV2944 cells, and, 24 to 48 hours later, the cells were suspended in phosphate buffer. Using a flow cytometer (FACS Aria, BD Biosciences), the OV2944 cells expressing the fluorescent protein tdTomato shown in FIG. 13A to FIG. 13C were purified.

Observation of Metastasis to Liver

Experimental Example 13-1

Figure 14:
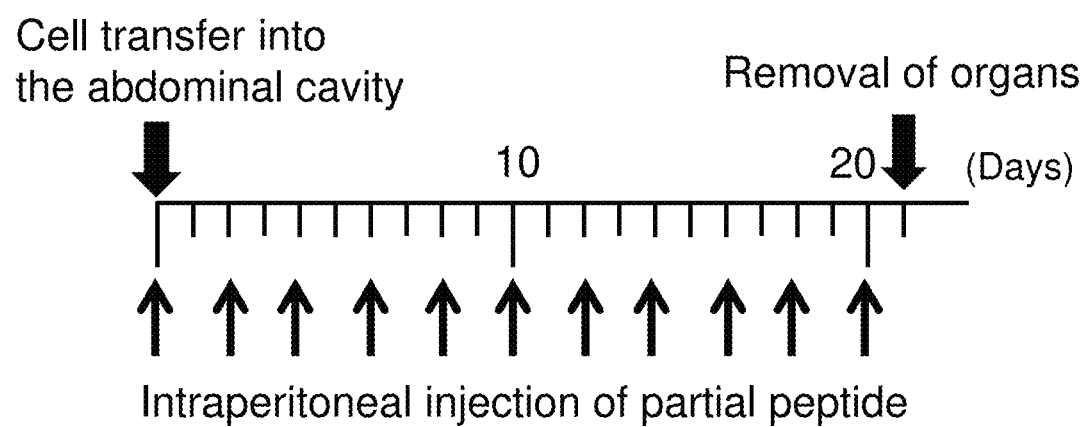
FIG. 14 shows a diagram illustrating the intraperitoneal injection schedule for partial peptide p6 in one experimental example in the present invention.

The purified OV2944 cells expressing the fluorescent protein tdTomato were transferred into the abdominal cavity of mice (B6C3F1 strain, 9 weeks old, female, CLEA Japan, Inc.) ($1\times10^5$ cells/mouse). According to the administration schedule shown in FIG. 14, partial peptide p6 was intraperitoneally injected (3 nmoles/two days; injection at 4 µg or less per dose on an every-other-day basis (injection at 20 µM in 150 µL per dose on an every-other-day basis)). On Day 21, the abdominal organs were removed, and OV2944 cells expressing the fluorescent protein tdTomato in the liver were observed using a fluorescence stereomicroscope OV110 (Olympus Corporation).

Experimental Example 13-2

An experiment was carried out in the same manner as in Experimental Example 13-1 except that partial peptide p1 was used as a control peptide, instead of partial peptide p6.

[Results]

Figures 2, 15:
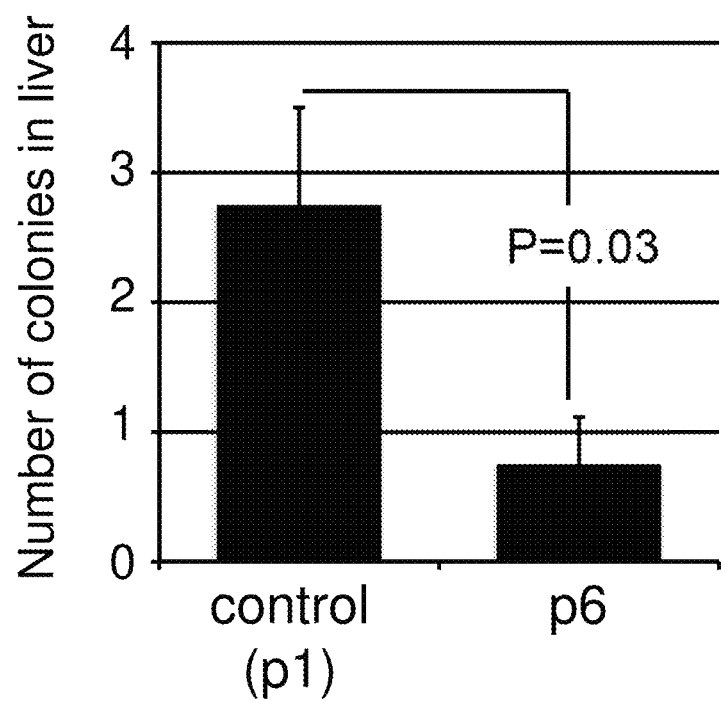

The obtained micrographs are shown in FIG. 15-1A to FIG. 15-1C. FIG. 15-1A shows comparison between Experimental Example 13-1 and Experimental Example 13-2. FIG. 15-1B focuses on cell colonies. FIG. 15-1C shows a magnified image of the area surrounded by the white square in the fluorescence image in FIG. 15-1B. The number of colonies was counted, and a significant difference was analyzed by unpaired Student t-test. The results are shown in FIG. 15-2.

In the case where partial peptide p6 was used, the number of colonies in the liver was significantly smaller than in the case where control peptide p1 was used.

Experimental Example 14-1, Experimental Example 14-2

(Analysis of Survival after Cell Transfer)

Intraperitoneal injection was carried out in the same manner as in Experimental Example 13-1 and Experimental Example 13-2, and survival analysis was carried out thereafter to provide Experimental Example 14-1 and Experimental Example 14-2. For the survival curve according to the Kaplan Meier method, a significant difference was analyzed by log-rank test.

[Results]

Figures 1, 16:
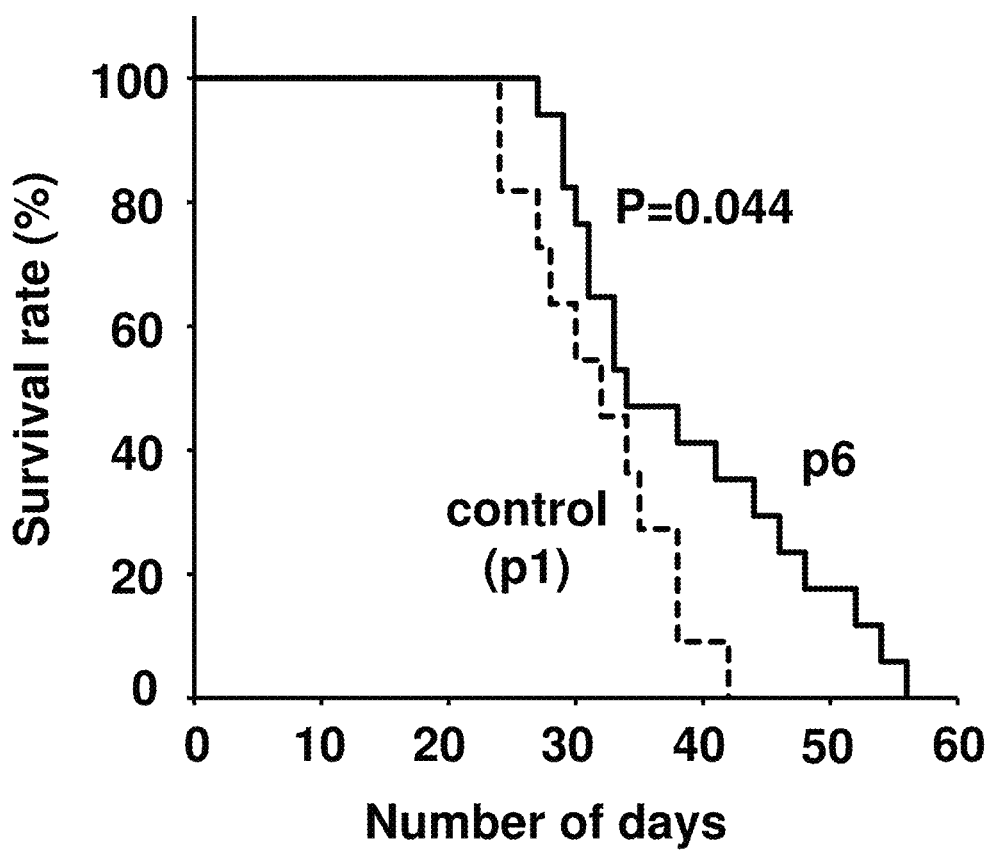
Figures 2, 16:
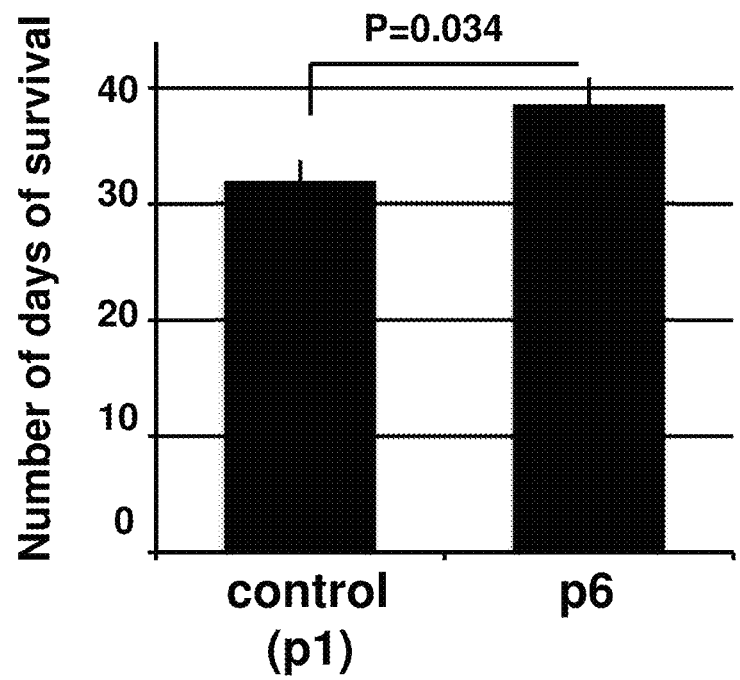

The results are shown in FIG. 16-1 and FIG. 16-2. It was found that partial peptide p6 significantly suppresses a decrease in the survival rate of mice to which OV2944 cells were transferred into the abdominal cavity, compared to control peptide p1. More specifically, the average number of days of survival was 32 days in Experimental Example 14-2, and 38.5 days in Experimental Example 14-1, indicating an increase by 21% in Experimental Example 14-1 relative to Experimental Example 14-2.

Non-patent Document 1, which is a conventional technique, reported that administration of paclitaxel at 20 mg/kg (twice a week, for two weeks) increased the average number of days of survival by about 20%. In the present invention, an equivalent increase in the average number of days of survival was found even with an amount of as small as about ¹⁄₆₀ compared to paclitaxel, indicating a remarkable effect of the present invention also from this point of view.

5. Experimental Examples Using Human Cancer Tissues

Cell Binding Experiment 1

Experimental Example 15-1

Figures 1, 17:
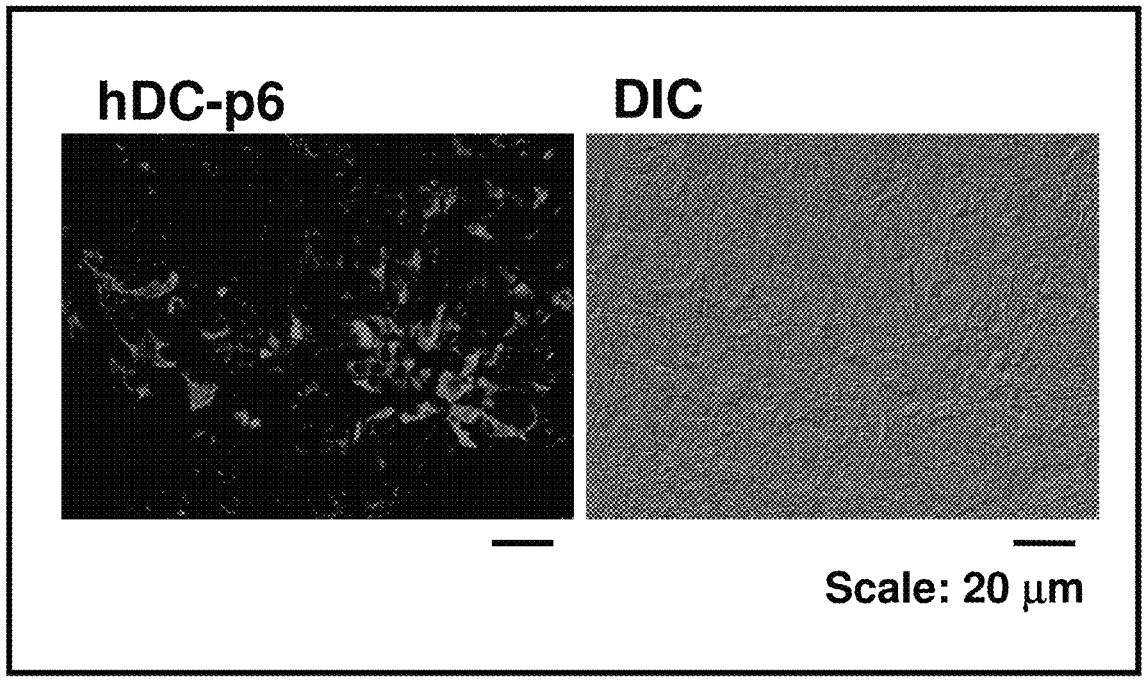
Figures 2, 17:
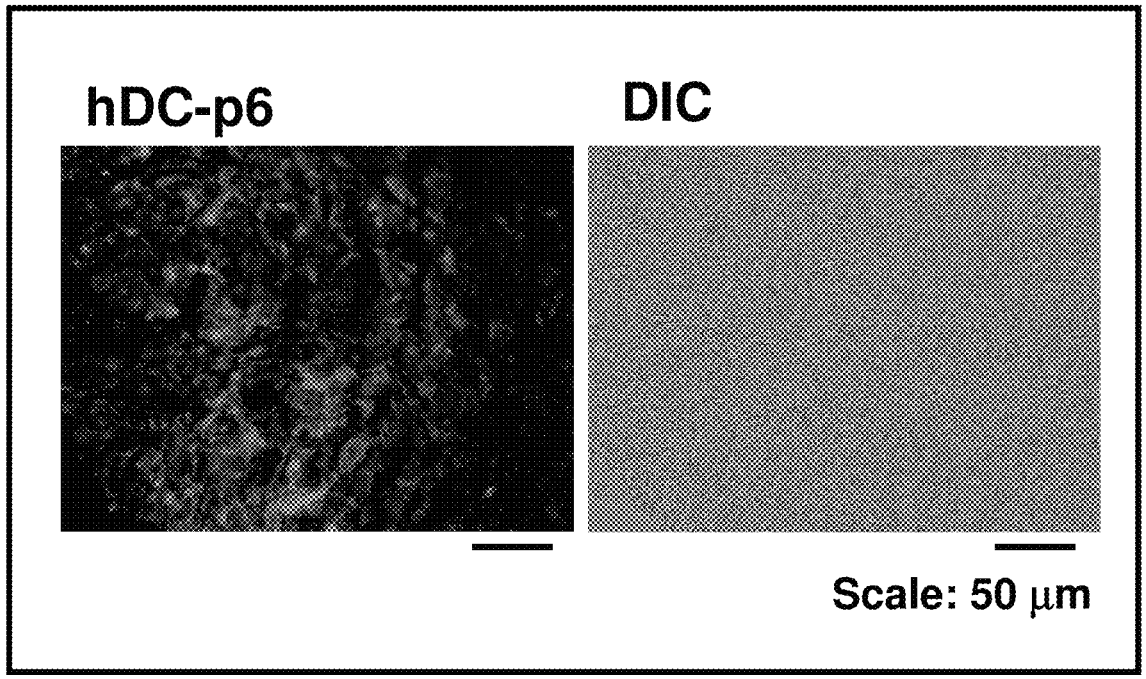
Figures 3, 17:
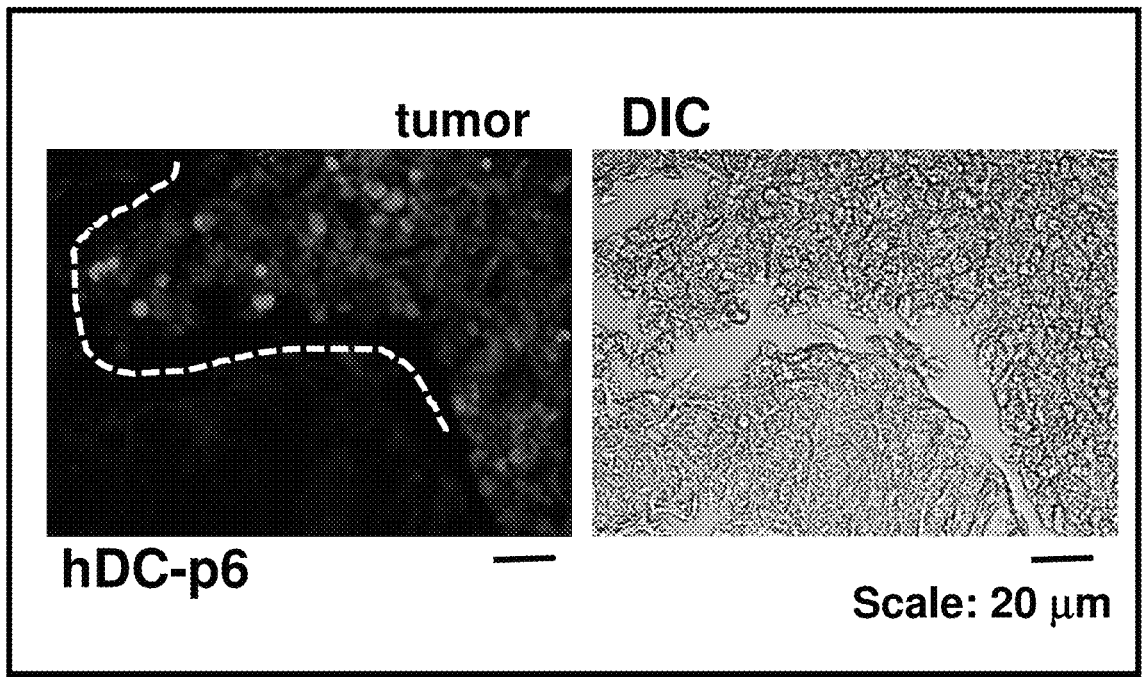
Figures 4, 17:
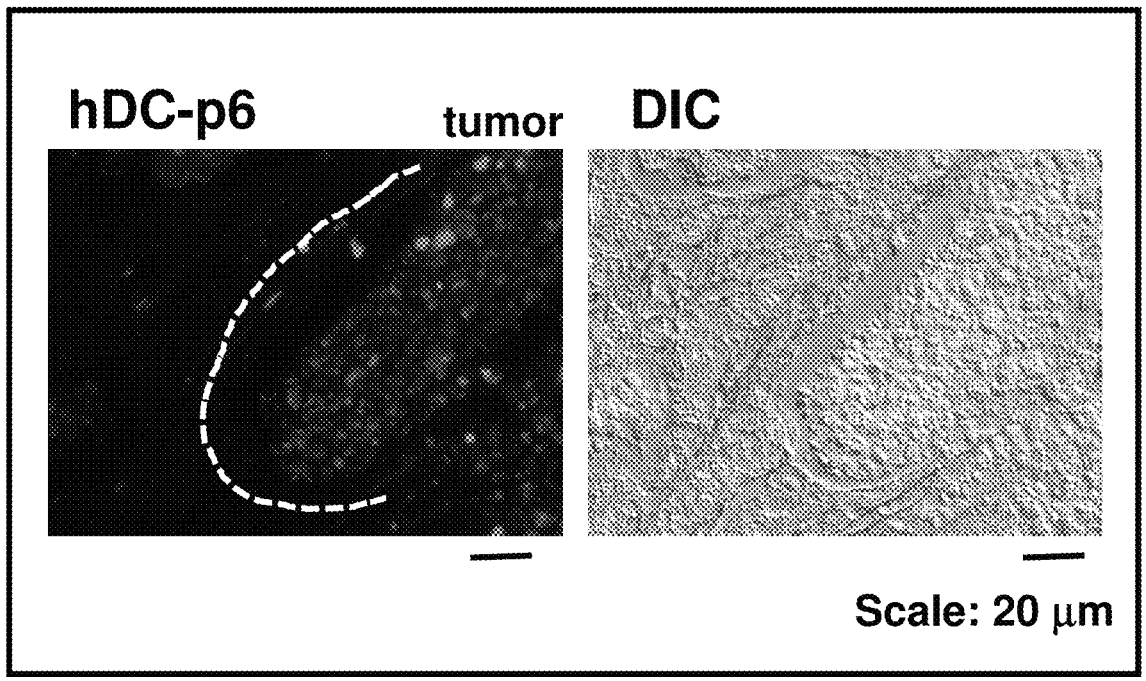
Figures 5, 17:
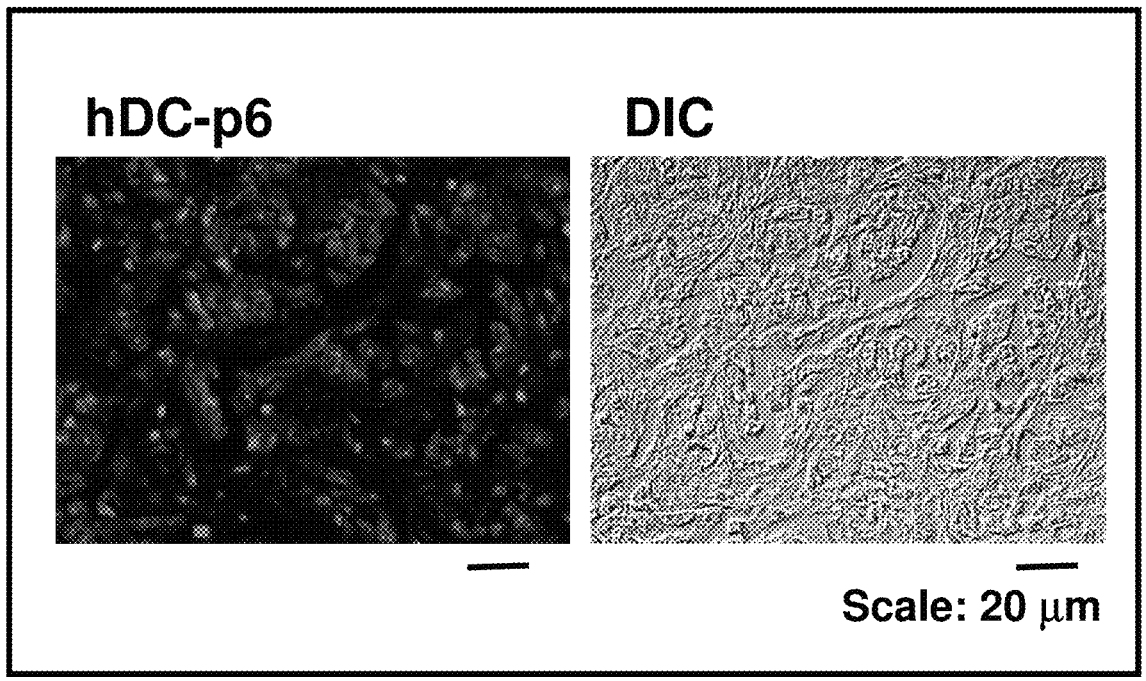
Figures 6, 17:
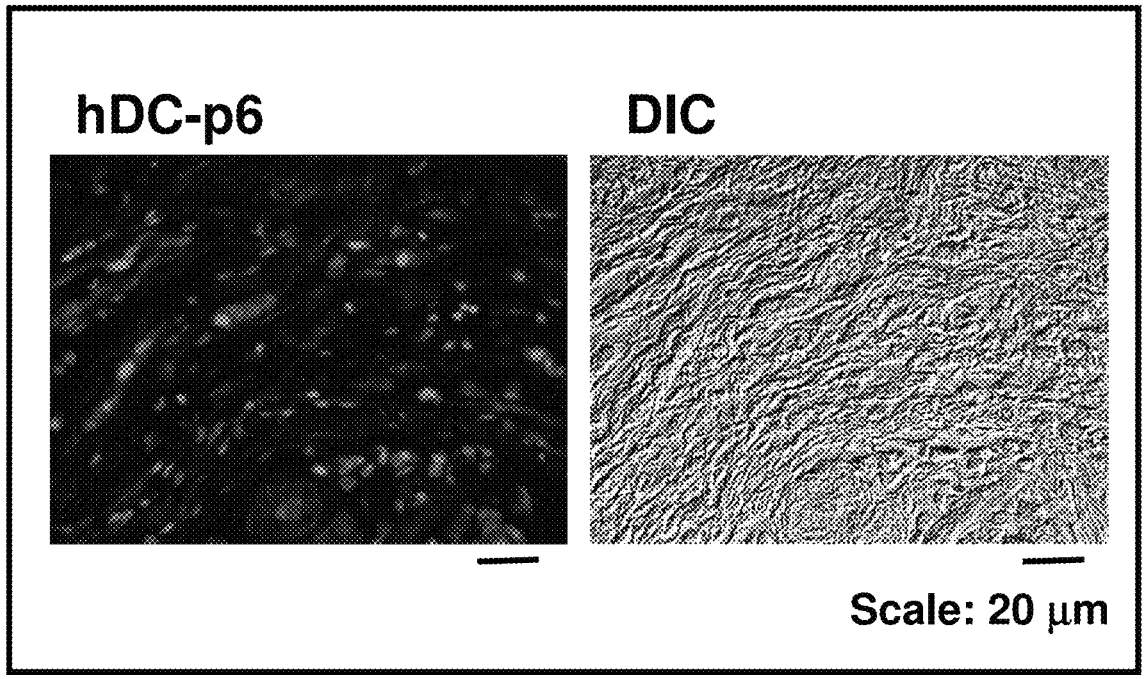
Figures 7, 17:
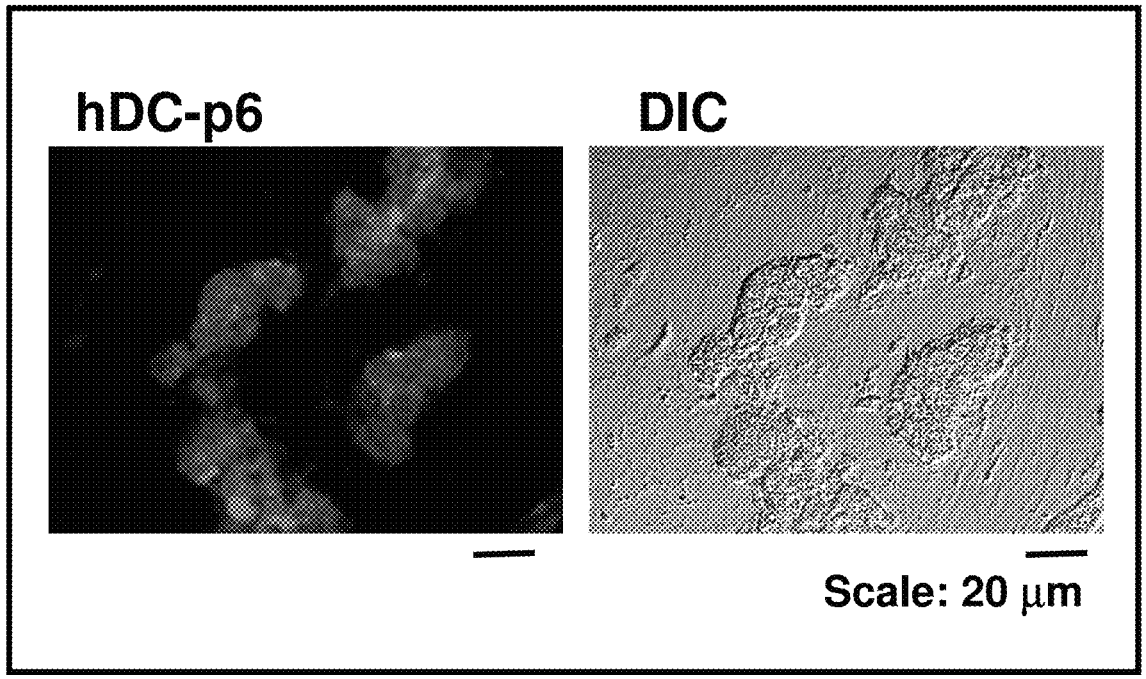
Figures 8, 17:
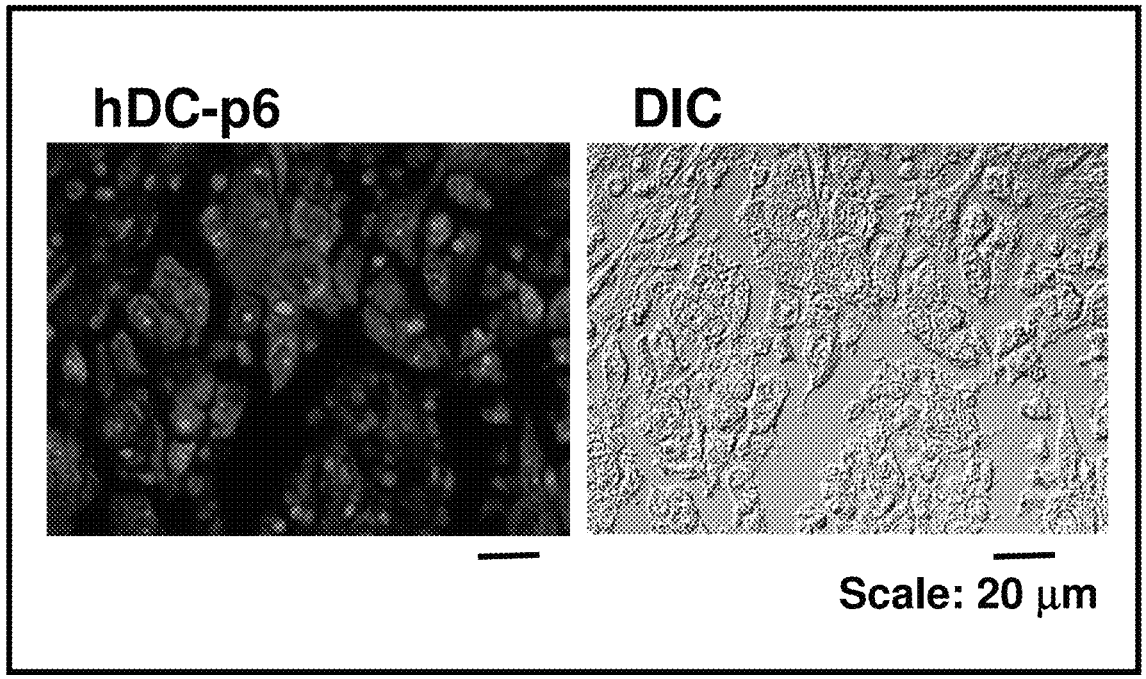
Figures 9, 17:
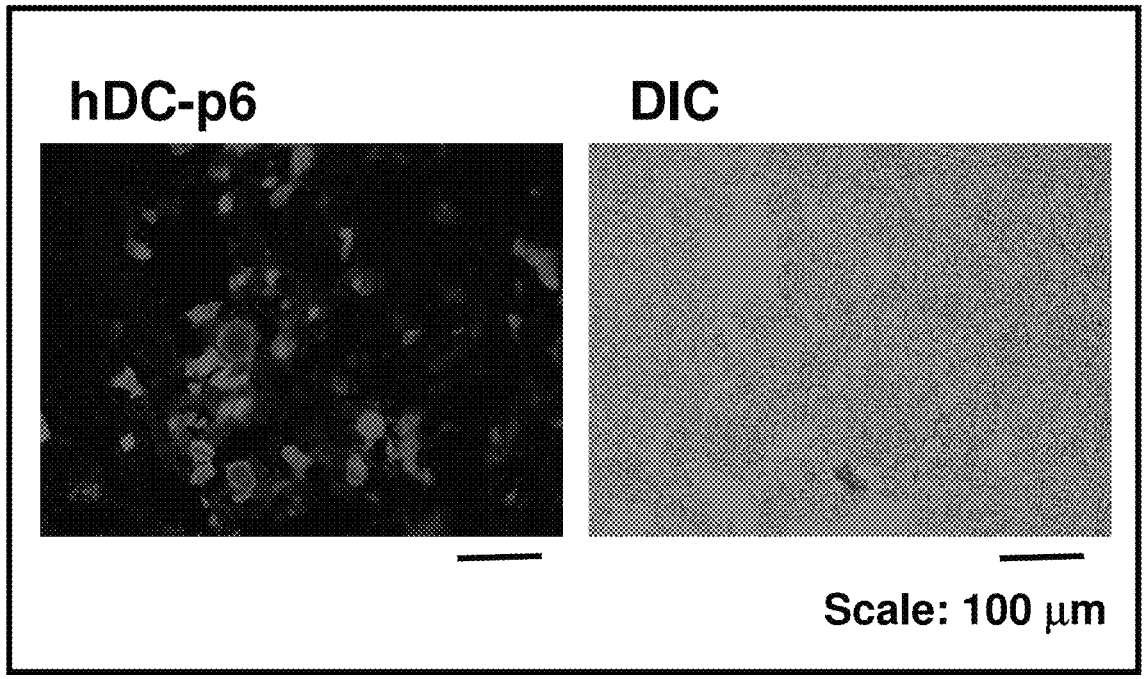
Figures 10, 17:
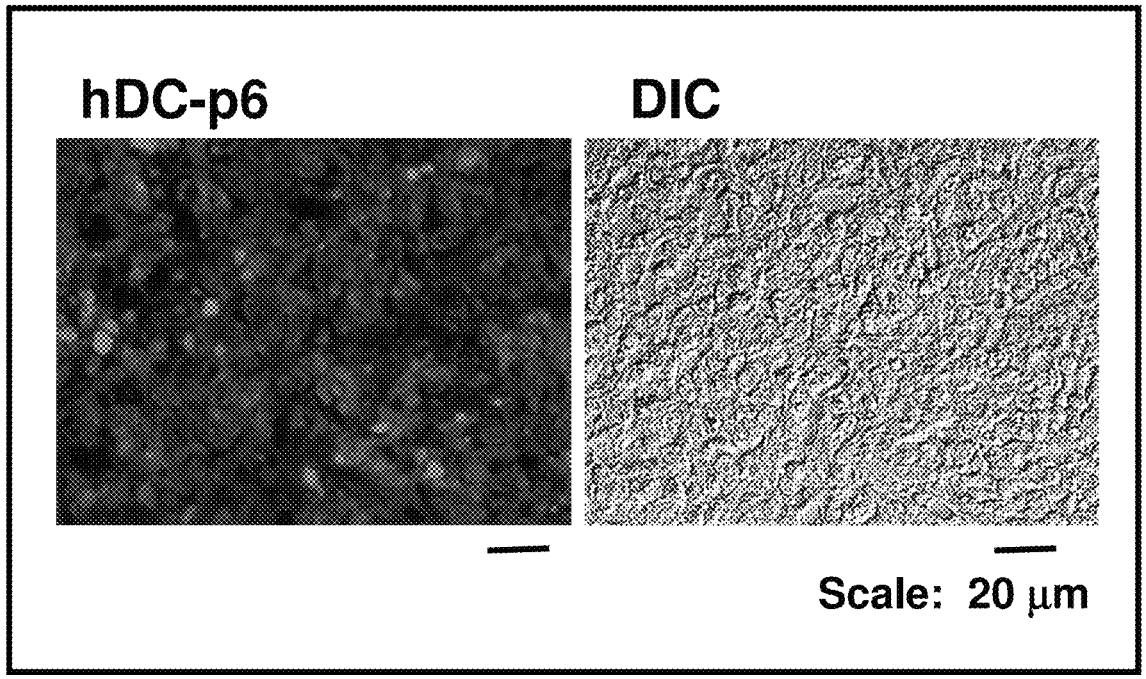
Figures 11, 17:
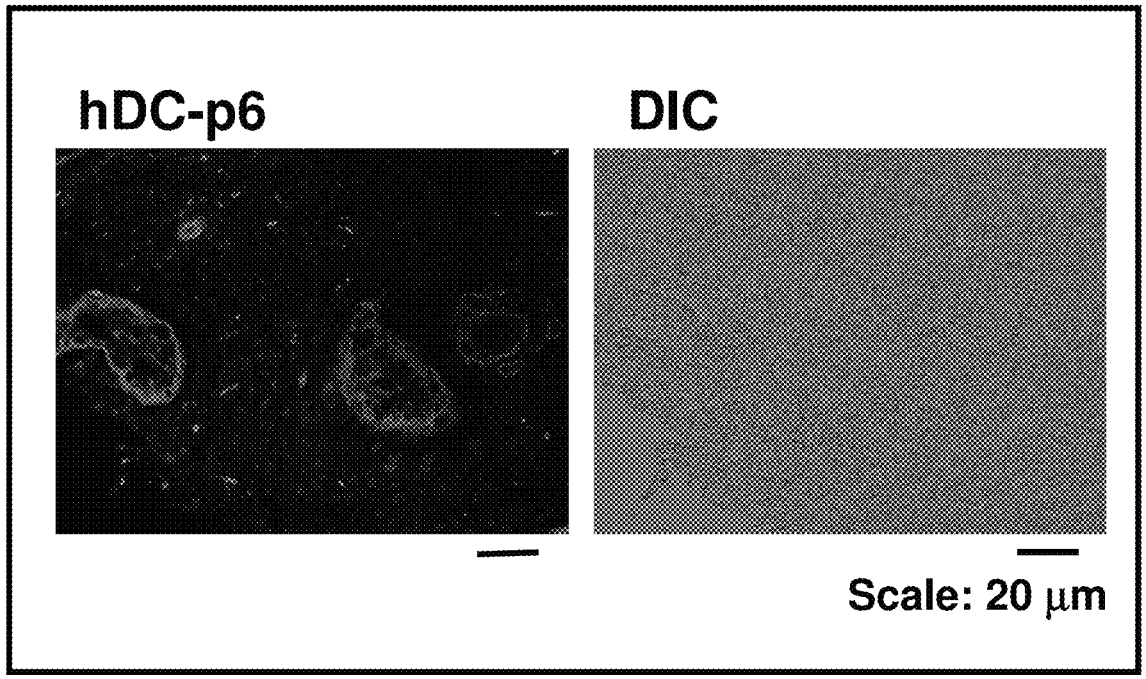
Figures 12, 17:
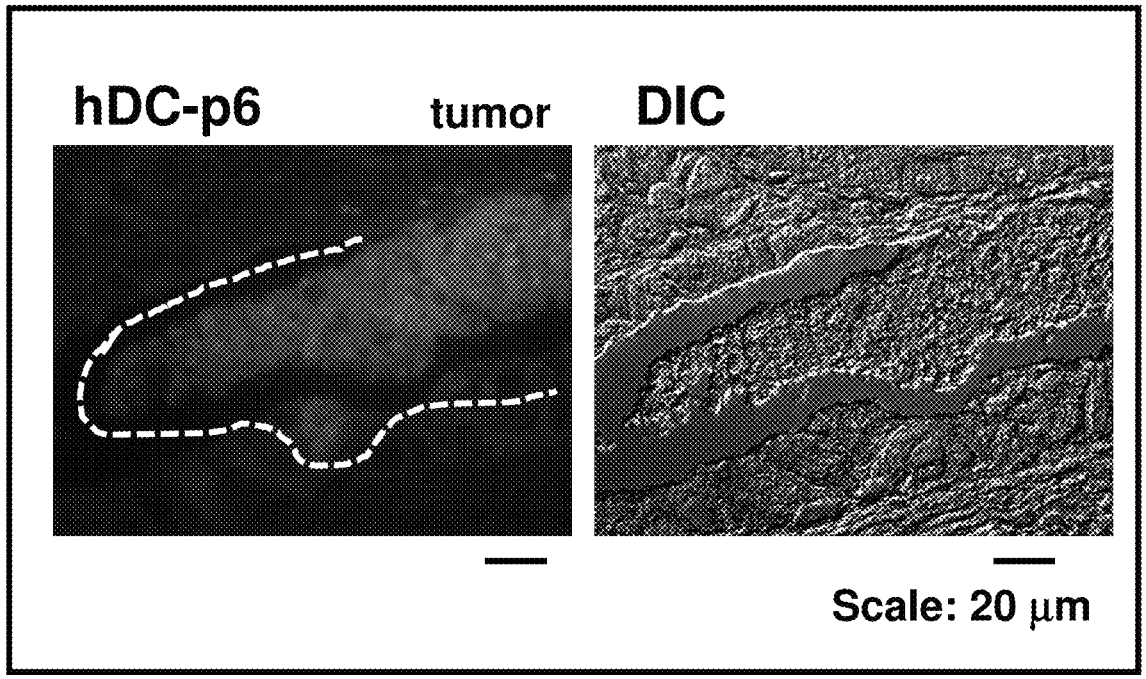

A paraffin section derived from a human ovarian cancer tissue (US Biomax Inc.) as a target was subjected to deparaffinization treatment, antigen retrieval treatment (98° C., 30 minutes), and blocking treatment (10% BSA, 37° C., 1 hour), followed by reaction (4° C., overnight) with partial peptide hDC-p6 (5 µM) of human dicalcin fluorescently labeled with rhodamine. After washing, analysis was carried out using a fluorescence microscope (Olympus Corporation). The result is shown in FIG. 17-1.

Experimental Example 15-2

An experiment was carried out in the same manner as in Experimental Example 15-1 except that a paraffin section derived from a human prostate cancer tissue (US Biomax Inc.) was used as a target. The result is shown in FIG. 17-2.

Experimental Example 15-3

An experiment was carried out in the same manner as in Experimental Example 15-1 except that a paraffin section derived from a human colorectal (colon) cancer tissue (US Biomax Inc.) was used as a target. The result is shown in FIG. 17-3. The white dotted line indicates the border between the tumor area and the normal area.

Experimental Example 15-4

An experiment was carried out in the same manner as in Experimental Example 15-1 except that a paraffin section derived from a human colorectal (rectal) cancer tissue (US Biomax Inc.) was used as a target. The result is shown in FIG. 17-4. The white dotted line indicates the border between the tumor area and the normal area.

Experimental Example 15-5

An experiment was carried out in the same manner as in Experimental Example 15-1 except that a paraffin section derived from a human breast cancer (breast ductal carcinoma) tissue (US Biomax Inc.) was used as a target. The result is shown in FIG. 17-5.

Experimental Example 15-6

An experiment was carried out in the same manner as in Experimental Example 15-1 except that a paraffin section derived from a human breast cancer (invasive lobular carcinoma) tissue (US Biomax Inc.) was used as a target. The result is shown in FIG. 17-6.

Experimental Example 15-7

An experiment was carried out in the same manner as in Experimental Example 15-1 except that a paraffin section derived from a human breast cancer (mucinous carcinoma) tissue (US Biomax Inc.) was used as a target. The result is shown in FIG. 17-7.

Experimental Example 15-8

An experiment was carried out in the same manner as in Experimental Example 15-1 except that a paraffin section derived from a human breast cancer (medullary carcinoma) tissue (US Biomax Inc.) was used as a target. The result is shown in FIG. 17-8.

Experimental Example 15-9

An experiment was carried out in the same manner as in Experimental Example 15-1 except that a paraffin section derived from a human renal cancer tissue (US Biomax Inc.) was used as a target. The result is shown in FIG. 17-9.

Experimental Example 15-10

An experiment was carried out in the same manner as in Experimental Example 15-1 except that a paraffin section derived from a human lung cancer (small cell carcinoma) tissue (US Biomax Inc.) was used as a target. The result is shown in FIG. 17-10.

Experimental Example 15-11

An experiment was carried out in the same manner as in Experimental Example 15-1 except that a paraffin section derived from a human brain glioma tissue (US Biomax Inc.) was used as a target. The result is shown in FIG. 17-11.
[Results]
It was found that partial peptide hDC-p6 binds to cancer cells of any of these tissues.

Cell Binding Experiment 2

Experimental Example 16-1

An experiment was carried out in the same manner as in Experimental Example 15-3 except that a paraffin section derived from a human colorectal (colon) cancer tissue (US Biomax Inc.) was subjected to the blocking treatment and the peptide reaction at the same time (10% BSA, partial peptide hDC-p6, 37° C., 1 hour). The result is shown in FIG. 17-12.
[Results]
In FIG. 17-12, the white dotted line indicates the border between the tumor area and the normal area. By testing the fluorescence positive reaction of partial peptide hDC-p6, the tumor area could be determined. Furthermore, it was found that a relatively equivalent result can be obtained even by carrying out the reaction together with the blocking treatment, and reducing the reaction time from overnight to one hour to shorten the time for obtaining the result. This indicates the convenience of partial peptide hDC-p6 as a determination agent.

6. Identification of Target Molecule of Partial Peptide p6 Using Mouse Ovarian Tumor Cell Line OV2944

Identification of Target Molecule Candidate in In Vitro Experiment

Experimental Example 17-1

Figure 18:
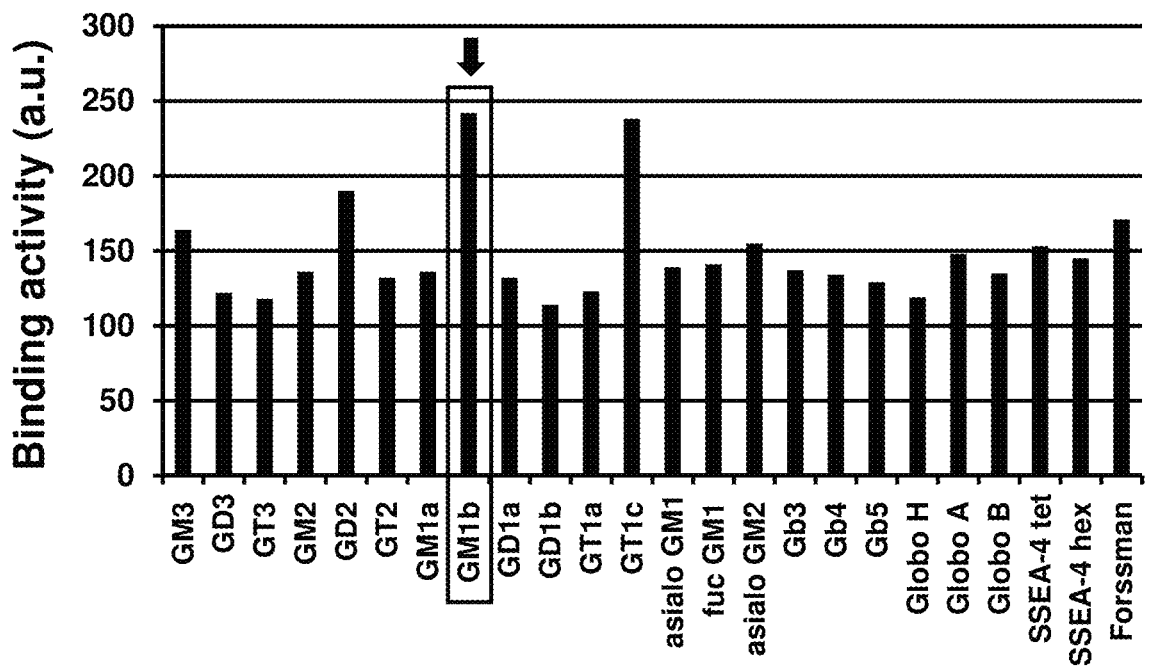
FIG. 18 shows a graph illustrating the results of a sugar chain binding experiment in one experimental example in the present invention.

A glycolipid sugar chain array (Sumitomo Bakelite Co., Ltd.) having various sugar chains immobilized on a slide was subjected to blocking treatment with 10% BSA, and reacted (4° C., overnight) with fluorescently labeled partial peptide p6 (5 µM) of mouse dicalcin. After washing, the binding abilities of partial peptide p6 to the glycolipid sugar chains were analyzed using an array scanner.
[Results]
The results are shown in FIG. 18. As a candidate of the target molecule to which partial peptide p6 binds, GM1b ganglioside was suggested.
(GM1b Inhibition Assay in Relation to Binding of Partial Peptide p6 to OV2944 Cells)

Experimental Example 18-1

Cultured OV2944 cells were fixed on a glass plate (4% paraformaldehyde/phosphate buffer, room temperature, 10 minutes), and treated with sheep serum. Thereafter, in the presence of GM1b (10, 100 µM), the cells were reacted (4° C., overnight) with partial peptide p6 (5 µM) of mouse dicalcin fluorescently labeled with tetramethylrhodamine (TMR), and an anti-CD44 antibody against CD44 as a membrane molecule control (together with an Alexa Fluor (registered trademark) 488-labeled anti-rat IgG antibody (Catalog No. A21208, Invitrogen) as a secondary antibody). After washing, analysis was carried out using a confocal microscope (Carl Zeiss).

Experimental Example 18-2

An experiment was carried out in the same manner as in Experimental Example 18-1 except that GM1b was absent.

Experimental Example 18-3

Further, an experiment was carried out in the same manner as in Experimental Example 18-1 and Experimental Example 18-2 for cases where GM1b was used alone at a concentration of 0, 10, or 100 µM, where GT1c was used alone at a concentration of 100 µM, and where GM1b and GT1c were used in combination at a concentration of 100 µM each.
[Results]
The results are shown in FIG. 19A to FIG. 19D. FIG. 19A and FIG. 19B show fluorescence images from Experimental Example 18-2 and Experimental Example 18-1, respectively. FIG. 19B shows the case where the GM1b concentration was 100 µM. For part of the anti-CD44 antibody fluorescence image (the area surrounded by the white line), the tetramethylrhodamine fluorescence image and the anti-CD44 antibody fluorescence image were synthesized to provide the fluorescence image labeled as "Merged".
FIG. 19C shows graphs illustrating the fluorescence intensity of tetramethylrhodamine and the fluorescence intensity of Alexa Fluor (registered trademark) 488 as measured from left to right along the white line (the white line which is not the white line showing a scale bar) in the fluorescence image labeled as "Merged" in FIG. 19A, and from upper left to lower right along the white line (the white line which is not the white line showing a scale bar) in the fluorescence image labeled as "Merged" in FIG. 19B. The fluorescence intensity of tetramethylrhodamine indicates binding of partial peptide p6 to an OV2944 cell. The fluorescence intensity of Alexa Fluor (registered trademark) 488 indicates the presence of CD44 as a control, and the location of the plasma membrane. According to the graphs, when GM1b was present in the medium, binding of partial peptide p6 to the OV2944 cell, especially the binding ability to the plasma membrane, remarkably decreased. This result suggests that the partial peptide p6 bound to GM1b in the medium, resulting in disappearance of binding to GM1b on the OV2944 cell membranes. Further, according to FIG. 19D, since the binding ability of partial peptide p6 to OV2944 cells did not change even in the presence of GT1c, it was shown that partial peptide p6 binds to GM1b rather than GT1c on the plasma membrane of OV2944 cells.

Suppression of Erk1/2 Signaling by Partial Peptide p6

Experimental Example 19-1

After addition of partial peptide p6 to OV2944 cells during culture (final concentration, 5 μM), the reaction was stopped sequentially (at Minutes 0, 5, 15, and 30) by addition of an electrophoresis loading buffer. The OV2944 cells were extracted and sonicated, and then analyzed for the activity of Erk1/2 by Western blotting. An antibody (Cell Signaling) against Erk1/2 protein in the phosphorylated state (that is, the activated state) (pErk1/2), or an antibody (Santa Cruz) against total Erk1/2 protein including the protein in the phosphorylated state and the protein in the dephosphorylated state (Erk1/2), was used therefor. The ratio between pErk1/2 and Erk1/2 (pErk/Erk) in the Western blot image was calculated, and the data were normalized by taking the value at time 0 as 1.

[Results]

The results are shown in FIG. 20A to FIG. 20B. FIG. 20A shows Western blot analysis with the pErk antibody or the Erk antibody. FIG. 20B shows quantification of the results of the Western blotting, and analysis of Erk activation over time.

Since time 0 in FIG. 20B corresponds to the steady state during culture, it was found that stimulation by partial peptide p6 alone (in the absence of GM1b) suppresses the Erk1/2 activity. It was found, on the other hand, that, when partial peptide p6 and GM1b are present, partial peptide p6 cannot bind to GM1b on the cell membranes, resulting in disappearance of the Erk-suppressing action. Thus, it was suggested that partial peptide p6 suppresses activation of Erk1/2 in OV2944 cells through binding to GM1b on the OV2944 cells, to decrease the migration ability and the metastatic ability of the cells.

The invention claimed is:

1. A method of inhibiting a human cancer cell metastasis, the method including administering to a human subject an effective amount of human dicalcin or a partial peptide thereof,
   wherein the amino acid sequence of human dicalcin consists of the amino acid sequence set forth in SEQ ID NO: 1; and
   wherein the partial peptide consists of:
   an amino acid sequence selected from the group consisting of SEQ ID Nos.: 3, 5, 6, 7, and 8, or
   an amino acid sequence selected from the group consisting of SEQ ID Nos. 3, 5, 6, 7, and 8 with the exception that one to three amino acids are added and the partial peptide has human cancer cell metastic inhibitory activity.

2. The method according to claim 1, wherein the cancer cell is a cell(s) of one or more cancers and/or tumors selected from the group consisting of ovarian cancer, prostate cancer, colorectal cancer, breast cancer, renal cancer, lung cancer, glioma, retinoblastoma, and lymphoma.

3. A peptide which consists of one amino acid sequence selected from SEQ ID NOs: 5, 6, 7, and 8, and which has human cancer cell metastasis inhibitory activity,
   a peptide which consists of the same amino acid sequence as one amino acid sequence selected from SEQ ID NOs: 3, 5, 6, 7, and 8 except that one to three amino acids are added, and which has human cancer cell metastasis inhibitory activity, or
   a pharmaceutically acceptable salt thereof.

4. A peptide which consists of one amino acid sequence selected from SEQ ID NOs: 5, 6, 7, and 8, and which binds to a human cancer cell,
   a peptide which consists of the same amino acid sequence as one amino acid sequence selected from SEQ ID NOs: 3, 5, 6, 7, and 8 except that one to three amino acids are added, and which binds to a human cancer cell, or
   a pharmaceutically acceptable salt thereof.

* * * * *